(12) United States Patent
Alvaro et al.

(10) Patent No.: US 8,093,268 B2
(45) Date of Patent: Jan. 10, 2012

(54) PHARMACEUTICAL COMPOSITIONS COMPRISING 2-METHOXY-5-(5-TRIFLUOROMETHYL-TETRAZOL-1-YL-BENZYL)-(2S-PHENYL PIPERIDIN-3S-YL-)

(75) Inventors: Giuseppe Alvaro, Verona (IT); Charles Large, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 89 days.

(21) Appl. No.: 12/524,434

(22) PCT Filed: Jan. 21, 2008

(86) PCT No.: PCT/EP2008/050621
§ 371 (c)(1),
(2), (4) Date: Jul. 24, 2009

(87) PCT Pub. No.: WO2008/090114
PCT Pub. Date: Jul. 31, 2008

(65) Prior Publication Data
US 2010/0113521 A1    May 6, 2010

(30) Foreign Application Priority Data

Jan. 24, 2007  (GB) .................................. 0701364.2
Jan. 24, 2007  (GB) .................................. 0701365.9
Jan. 24, 2007  (GB) .................................. 0701366.7
Jan. 24, 2007  (GB) .................................. 0701367.5
Jan. 24, 2007  (GB) .................................. 0701368.3

(51) Int. Cl.
*A61K 31/454* (2006.01)
(52) U.S. Cl. ..................................... 514/326
(58) Field of Classification Search ................... 514/326
See application file for complete search history.

(56) References Cited

U.S. PATENT DOCUMENTS 5,804,596 A * 9/1998 Majeed et al. ................. 514/455
5,843,966 A * 12/1998 Armour et al. ................. 514/326

FOREIGN PATENT DOCUMENTS

| WO | 9508549 A1 | 3/1995 |
| WO | 2004083190 A1 | 9/2004 |
| WO | 2004091617 A1 | 10/2004 |
| WO | 2004092140 A1 | 10/2004 |
| WO | 2004094395 A2 | 11/2004 |
| WO | 2005102336 A1 | 11/2005 |

OTHER PUBLICATIONS

Souillac et al. Characterization of delivery systems, differential scanning caloimery, pp. 217-218 (in Encyclopedia of Controlled Drug Delivery, 1999, John Wiley & Sons, pp. 212-227).*
Vippagunta et al. Advanced Drug Delivery Reviews, 48 (2001) pp. 3-26.*

* cited by examiner

*Primary Examiner* — Jennifer M Kim
(74) *Attorney, Agent, or Firm* — Kathryn L. Coulter

(57) ABSTRACT

The present invention relates to pharmaceutical compositions comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, as a combined preparation for simultaneous or sequential administration and to the use of such compositions in the treatment of certain disorders, including epilepsy, mood disorders and pain.

4 Claims, 9 Drawing Sheets

PHARMACEUTICAL COMPOSITIONS COMPRISING 2-METHOXY-5-(5-TRIFLUOROMETHYL-TETRAZOL-1-YL-BENZYL)-(2S-PHENYL PIPERIDIN-3S-YL-)

This application is filed pursuant to 35 U.S.C. §371 as a United States National Phase Application of International Patent Application Serial No. PCT/EP2008/050621 filed Jan. 21, 2008, which claims priority from Great Britain Application Nos. 0701364.2; 0701365.9; 0701366.7; 0701367.5; and 0701368.3 filed in the United Kingdom on Jan. 24, 2007.

The present invention relates to pharmaceutical compositions comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, as a combined preparation for simultaneous or sequential administration. The invention further relates to the use of such compositions in the treatment of certain disorders, including epilepsy, mood disorders and pain.

Substance P is a short-chain polypeptide that functions as a neurotransmitter and a neuromodulator. It belongs to the tachykinin neuropeptide family. In the central nervous system Substance P has been associated with the regulation of mood disorders, anxiety, stress, reinforcement, neurogenesis, respiratory rhythm, neurotoxicity, nausea/emesis and pain. The endogenous receptor for Substance P is the neurokinin 1 receptor (NK1 receptor). A large number of NK1 receptor antagonists are known, including aprepitant (Emend™), which is marketed for use in the prevention of acute and delayed chemotherapy-induced nausea and vomiting and in the prevention of post operative nausea and vomiting. Other potential uses of NK1 receptor antagonists include treatment of anxiety and depression, pain, inflammatory diseases, overactive bladder, sleep disorders, allergic disorders, CNS disorders, skin disorders, cough and gastrointestinal disorders.

Voltage-gated sodium channels are responsible for the initial phase of the action potential, which is a wave of electrical depolarisation usually initiated at the soma of the neuron and propagated along the nerve axon to the terminals. At the terminals, the action potential triggers the influx of calcium and the release of neurotransmitter. Some sodium channel blockers, such as lamotrigine and carbamazepine are used to treat epilepsy. In this case, partial inhibition of voltage-gated sodium channels reduces neuronal excitability and reduces seizure propagation. A key feature of these drugs is their use-dependent mechanism of action. The drugs are thought to stabilise an inactivated configuration of the channel that is adopted rapidly after the channel opens. This inactivated state provides a refractory period before the channel returns to its resting (closed) state ready to be reactivated. As a result, use-dependent sodium channel blockers retard the firing of neurons at high frequency, for example in response to painful stimuli, and will help to prevent repetitive firing during periods of prolonged neuronal depolarisation that might occur, for example, during a seizure. Action potentials triggered at low frequencies, for example in the heart, will not be significantly affected by these drugs, although the safety margin differs in each case, since at high enough concentrations each of these drugs is capable of blocking the resting or open states of the channels.

Drugs that block voltage-gated sodium channels in a use-dependent manner are also used in the treatment of bipolar disorder, either to reduce symptoms of mania or depression, or as mood stabilisers to prevent the emergence of mood episodes. Clinical and preclinical evidence also suggests that use-dependent sodium channel blockers may help to reduce the symptoms of schizophrenia. It is hypothesised that efficacy in these psychiatric disorders may result in part from a reduction of excessive glutamate release. The reduction in glutamate release is thought to be a consequence of use-dependent sodium channel inhibition in key brain areas, such as the frontal cortex. However, interaction with voltage-gated calcium channels may also contribute to the efficacy of these drugs.

Lamotrigine is an effective anticonvulsant that is also indicated in the US for the prevention of mood episodes in patients with bipolar I disorder. However, the efficacy of the drug in an acute setting is limited by the need for a 4-6 week dose-titration to avoid rash. In addition, lamotrigine and other sodium channel blockers are limited in the range of doses that can be explored to achieve efficacy due to the appearance of CNS side-effects.

The aim of the present invention is to identify new pharmaceutical compositions that allow an improved clinical efficacy with respect to the individual components when administered alone.

A further aim of the present invention is to identify new pharmaceutical compositions that allow the use of a decreased dose of the active ingredient or ingredients, in order to achieve an improved tolerability profile, i.e. reduce side effects.

A solution provided by the present invention is a pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, as a combined preparation for simultaneous or sequential administration.

In one embodiment, a solution provided by the present invention is a pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, wherein at least one of them is at sub therapeutic dose, as a combined preparation for simultaneous or sequential administration.

Thus, in a first aspect the invention provides a pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, as a combined preparation for simultaneous or sequential administration.

In one embodiment, the invention provides a pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, wherein at least one of them is at sub therapeutic dose, as a combined preparation for simultaneous or sequential administration.

Figure 1:
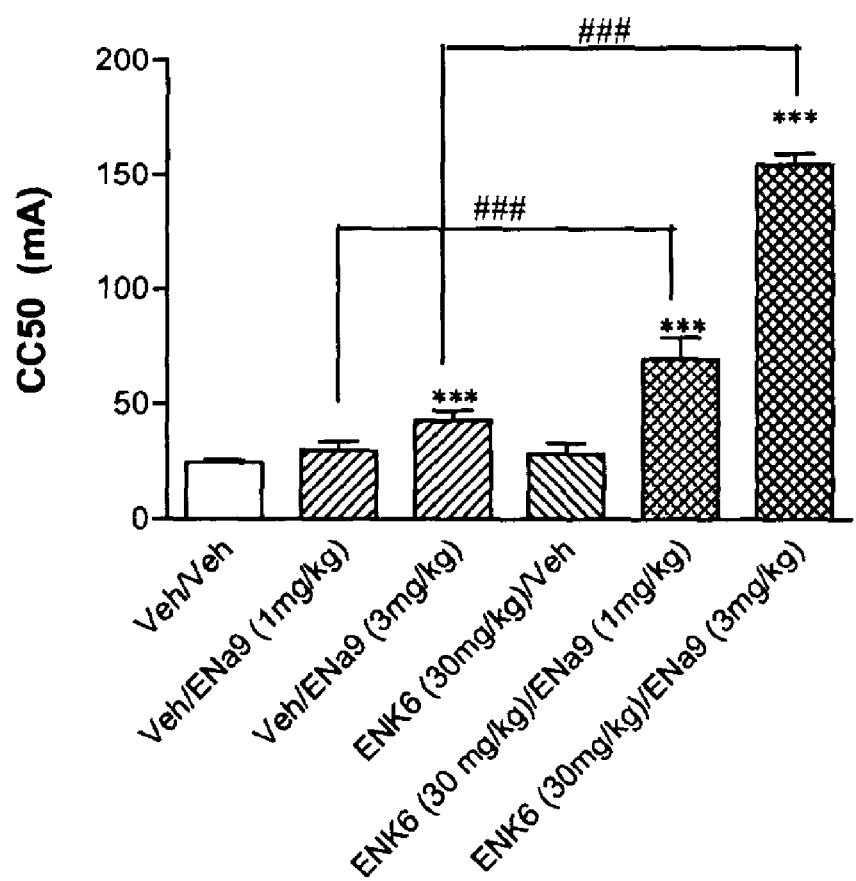
FIG. 1: Effects of ENa9 and ENK6 in the rat MEST model. ENK6 (30 mg/kg, ip, 60 min ptt); ENa9 (1.0 & 3.0 mg/kg, sc, 30 min ptt). ***$p<0.001$ vs corr vehicle, Wilcoxon Test. ### $p<0.001$ Vs corr vehicle/ENa9 group, t-test.

Pharmaceutical compositions according to the present invention comprise the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, wherein one of them may be used at sub therapeutic dose, together with one or more pharmaceutically acceptable carriers or excipients and optionally other therapeutic agents. The carrier(s) must be acceptable in the sense of being compatible with the other ingredients of the formula and not deleterious to the recipient thereof. When the individual components of the composition are administered separately, they are generally each presented as a pharmaceutical compositions. The references hereinafter to composition refer, unless otherwise stated, to compositions comprising either both the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, or only one component thereof.

A subtherapeutic dose is intended to mean a dose of a drug below that required to produce significant clinical benefit for the patient when administered alone.

In a further aspect, the invention provides a method of treating a human or animal subject suffering from epilepsy, mood disorders or pain, which comprises administering to said subject an effective amount of a pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof and a sodium channel blocker.

In another embodiment, the invention provides a method of treating a human or animal subject suffering from epilepsy, mood disorders or pain, which comprises administering to said subject an effective amount of a pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, wherein at least one of them is at sub therapeutic dose.

In a further aspect the invention provides a pharmaceutical composition comprising the NK1 receptor antagonist [2-Methoxy-5-(5-trifluoromethyl-tetrazol-1-yl)-benzyl]-(2S-phenyl-piperidin-3S-yl)-amine or a pharmaceutically acceptable salt or solvate thereof, and a sodium channel blocker, for use in therapy.

In a further embodiment, the invention provides a pharmaceutical composition comprising the NK1 receptor antagonist [2-Methoxy-5-(5-trifluoromethyl-tetrazol-1-yl)-benzyl]-(2S-phenyl-piperidin-3S-yl)-amine or a pharmaceutically acceptable salt or solvate thereof, and a sodium channel blocker, wherein at least one of them is at sub therapeutic dose, for use in therapy.

In one aspect, the invention provides a pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, for use in the treatment of epilepsy, mood disorders or pain.

In another embodiment the invention provides a pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, wherein at least one of them is at sub therapeutic dose, for use in the treatment of epilepsy, mood disorders or pain.

In a still further aspect, the invention provides the use of a pharmaceutical composition, comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and sodium channel blocker, in the manufacture of a medicament for the treatment of epilepsy, mood disorders or pain.

In another embodiment, the invention provides the use of a pharmaceutical composition, comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, wherein at least one of them is at sub therapeutic dose, in the manufacture of a medicament for the treatment of epilepsy, mood disorders or pain.

In an additional aspect, the invention provides the use of a pharmaceutical composition, comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, for the treatment of epilepsy, mood disorders or pain.

In an additional embodiment, the invention provides the use of a pharmaceutical composition, comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a sodium channel blocker, wherein at least one of them is at sub therapeutic dose, for the treatment of epilepsy, mood disorders or pain.

Within the context of the present invention, the term epilepsy is intended to include Seizure disorders and epilepsy syndromes. The various types of the Epilepsy and seizures mentioned hereinbelow are contemplated as part of the present invention: partial onset seizures (replacing temporal lobe epilepsy, neocortical epilepsy and Rasumssen's), generalized onset seizures, the seizures of the Lennox Gastaut syndrome (tonic, atonic, myoclonic, atypical absence and generalized tonic-clonic), absence seizure syndromes and juvenile myoclonic epilepsy.

Pharmaceutical compositions of the invention may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Further diseases or conditions that may be treated by administration of the pharmaceutical compositions of the invention are selected from the list consisting of: psychotic disorders, mood disorders and pain.

Within the context of the present invention, the terms describing the Psychiatric indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes:
i) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Within the context of the present invention, the term "mood disorders" includes:
i) Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

The term "mood disorders" also includes mood disorders in Epilepsy patients.

Within the context of the present invention, the term "pain" includes: chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with cluster and chronic daily headache; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; dysmenorrhea; neuralgia; fibromyalgia syndrome; complex regional pain syndrome (CRPS types I and II); neuropathic pain syndromes (including diabetic neuropathy; chemotherapeutically induced neuropathic pain; sciatica; non-specific lower back pain; multiple sclerosis pain; HIV-related neuropathy; post-herpetic neuralgia; trigeminal neuralgia); and pain resulting from physical trauma, amputation, cancer, toxins or chronic inflammatory conditions.

In one embodiment, the "mood disorder" which may be treated by administration of the pharmaceutical compositions of the invention is a bipolar disorder.

It will be appreciated that references herein to "treatment" extend to prophylaxis, prevention of recurrence and suppression or amelioration of symptoms (whether mild, moderate or severe) as well as the treatment of established conditions.

In one embodiment, the pharmaceutical composition of the invention as herein above defined comprises a Sodium Channel blocker selected from the group consisting of: fosphenytoin (Cerebyx™, Prodilantin™, Pro-Epanutin™ or Cereneu™); oxcarbazepine (Trileptal™, Oxrate™ or Wockhardt™); phenytoin; carbamazepine (Carbatrol, Equetro™); lidocaine (ALGRX-3268); Safinamide (NW-1015); Ralfinamide (NW-1029); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and 5-(4-{[(2-fluorophenyl)methyl]oxy}phenyl)-prolinamide, or a pharmaceutically acceptable salt or solvate thereof.

In a further embodiment, the pharmaceutical composition of the invention as hereinabove defined comprises a Sodium Channel blocker selected from the group consisting of fosphenytoin (Cerebyx™, Prodilantin™, Pro-Epanutin™ or Cereneu™), oxcarbazepine (Trileptal™, Oxrate™ or Wockhardt™), phenytoin, carbamazepine (Carbatrol, Equetro™), lidocaine (ALGRX-3268), Safinamide (NW-1015) and Ralfinamide (NW-1029).

In a further embodiment, the pharmaceutical composition of the invention as herein above defined comprises a Sodium Channel blocker selected from the group consisting of:
3,5-diamino-6-(2,3-dichlorophenyl)-1,2,4-triazine;
R(−)-2,4-diamino-5-(2,3-dichlorophenyl)-6-fluoromethylpyrimidine;
(2R,5R)-2-(4-{[(2-fluorophenyl)methyl]oxy}phenyl)-1,7-diazaspiro[4.4]nonan-6-one;
(2R,5R)-2-(4-{[(2-fluorophenyl)methyl]oxy}phenyl)-7-methyl-1,7-diazaspiro[4.4]nonan-6-one;
5-(4-{[(2-fluorophenyl)methyl]oxy}phenyl)-prolinamide;
and pharmaceutically acceptable salts or solvates thereof.

In a still further embodiment, the pharmaceutical composition of the invention as herein above defined comprises a Sodium Channel blocker selected from the group consisting of:
3,5-diamino-6-(2,3-dichlorophenyl)-1,2,4-triazine;
R(−)-2,4-diamino-5-(2,3-dichlorophenyl)-6-fluoromethylpyrimidine;
and pharmaceutically acceptable salts or solvates thereof.

In an additional further embodiment, the pharmaceutical composition of the invention as herein above defined comprises a Sodium Channel blocker which is 3,5-diamino-6-(2, 3-dichlorophenyl)-1,2,4-triazine or a pharmaceutically acceptable salt or solvate thereof.

Compound 3,5-diamino-6-(2,3-dichlorophenyl)-1,2,4-triazine and pharmaceutically acceptable salts and solvates thereof are described in EP granted Patent EP0021121B and in U.S. Pat. No. 4,602,017. The disclosure of this reference is incorporated herein in its entirety. Compound 3,5-diamino-6-(2,3-dichlorophenyl)-1,2,4-triazine and pharmaceutically acceptable salts and solvates thereof may be prepared by any method described in EP0021121B and U.S. Pat. No. 4,602,017.

In another embodiment, the pharmaceutical composition of the invention as herein above defined comprises a Sodium Channel blocker which is R(−)-2,4-diamino-5-(2,3-dichlorophenyl)-6-fluoromethylpyrimidine or a pharmaceutically acceptable salt or solvate thereof.

Compound R(−)-2,4-diamino-5-(2,3-dichlorophenyl)-6-fluoromethylpyrimidine and pharmaceutically acceptable salts and solvates thereof are described in PCT publication No. WO 97/9317, published 13 Mar. 1997. The disclosure of this reference is incorporated herein in its entirety. Compound R(−)-2,4-diamino-5-(2,3-dichlorophenyl)-6-fluoromethyl pyrimidine and pharmaceutically acceptable salts and solvates thereof may be prepared by any method described in WO 97/9317.

In one embodiment, the pharmaceutical composition of the invention comprises a Sodium Channel blocker, at subtherapeutic dose, selected from the group consisting of: fosphenytoin (Cerebyx™, Prodilantin™, Pro-Epanutin™ or Cereneu™); oxcarbazepine (Trileptal™, Oxrate™ or Wockhardt™); phenytoin; carbamazepine (Carbatrol, Equetro™); lidocaine (ALGRX-3268); Safinamide (NW-1015); Ralfinamide (NW-1029); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and 5-(4-{[(2-fluorophenyl)methyl]oxy}phenyl)-prolinamide, or a pharmaceutically acceptable salt or solvate thereof; and [2-Methoxy-5-(5-trifluoromethyl-tetrazol-1-yl)-benzyl]-(2S-phenyl-piperidin-3S-yl)-amine, or a pharmaceutically acceptable salt or solvate thereof.

In one embodiment, the pharmaceutical composition of the invention comprises a Sodium Channel blocker selected from the group consisting of: fosphenytoin (Cerebyx™, Prodilantin™, Pro-Epanutin™ or Cereneu™); oxcarbazepine (Trileptal™, Oxrate™ or Wockhardt™); phenytoin; carbamazepine (Carbatrol, Equetro™); lidocaine (ALGRX-3268); Safinamide (NW-1015); Ralfinamide (NW-1029); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and 5-(4-{[(2-fluorophenyl)methyl]oxy}phenyl)-prolinamide, or a pharmaceutically acceptable salt or solvate thereof; and [2-Methoxy-5-(5-trifluoromethyl-tetrazol-1-yl)-benzyl]-(2S-phenyl-piperidin-3S-yl)-amine, or a pharmaceutically acceptable salt or solvate thereof, at sub therapeutic dose.

In one embodiment, the pharmaceutical composition of the invention comprises a Sodium Channel blocker selected from the group consisting of: fosphenytoin (Cerebyx™, Prodilantin™, Pro-Epanutin™ or Cereneu™); oxcarbazepine (Trileptal™, Oxrate™ or Wockhardt™); phenytoin; carbamazepine (Carbatrol, Equetro™); lidocaine (ALGRX-3268); Safinamide (NW-1015); Ralfinamide (NW-1029); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and 5-(4-{[(2-fluorophenyl)methyl]oxy}phenyl)-prolinamide, or a pharmaceutically acceptable salt or solvate thereof; and [2-Methoxy-5-(5-trifluoromethyl-tetrazol-1-yl)-benzyl]-(2S-phenyl-piperidin-3S-yl)-amine, or a pharmaceutically acceptable salt or solvate thereof; such NK1 receptor antagonist and Sodium Channel blocker compounds being both administered at sub therapeutic dose.

In one embodiment, the pharmaceutical composition of the invention comprises 3,5-diamino-6-(2,3-dichlorophenyl)-1,2,4-triazine, or a pharmaceutically acceptable salt or solvate thereof, and [2-Methoxy-5-(5-trifluoromethyl-tetrazol-1-yl)-benzyl]-(2S-phenyl-piperidin-3S-yl)-amine, or a pharmaceutically acceptable salt or solvate thereof.

In a further embodiment the pharmaceutical composition of the invention comprises 3,5-diamino-6-(2,3-dichlorophenyl)-1,2,4-triazine, or a pharmaceutically acceptable salt or solvate thereof, at subtherapeutic dose and [2-Methoxy-5-(5-trifluoromethyl-tetrazol-1-yl)-benzyl]-(2S-phenyl-piperidin-3S-yl)-amine, or a pharmaceutically acceptable salt or solvate thereof.

In another embodiment the pharmaceutical composition of the invention comprises 3,5-diamino-6-(2,3-dichlorophenyl)-1,2,4-triazine, or a pharmaceutically acceptable salt or solvate thereof, and [2-Methoxy-5-(5-trifluoromethyl-tetrazol-1-yl)-benzyl]-(2S-phenyl-piperidin-3S-yl)-amine, or a pharmaceutically acceptable salt or solvate thereof, at subtherapeutic dose.

In one embodiment the pharmaceutical composition of the invention comprises R(−)-2,4-diamino-5-(2,3-dichlorophenyl)-6-fluoromethylpyrimidine, or a pharmaceutically acceptable salt or solvate thereof, and [2-Methoxy-5-(5-trifluoromethyl-tetrazol-1-yl)-benzyl]-(2S-phenyl-piperidin-3S-yl)-amine, or a pharmaceutically acceptable salt or solvate thereof.

In another embodiment the pharmaceutical composition of the invention comprises R(−)-2,4-diamino-5-(2,3-dichlorophenyl)-6-fluoromethylpyrimidine, or a pharmaceutically acceptable salt or solvate thereof, at subtherapeutic dose and [2-Methoxy-5-(5-trifluoromethyl-tetrazol-1-yl)-benzyl]-(2S-phenyl-piperidin-3S-yl)-amine, or a pharmaceutically acceptable salt or solvate thereof.

In a further embodiment, the pharmaceutical composition of the invention comprises R(−)-2,4-diamino-5-(2,3-dichlorophenyl)-6-fluoromethylpyrimidine, or a pharmaceutically acceptable salt or solvate thereof, and [2-Methoxy-5-(5-trifluoromethyl-tetrazol-1-yl)-benzyl]-(2S-phenyl-piperidin-3S-yl)-amine, or a pharmaceutically acceptable salt or solvate thereof, at subtherapeutic dose.

In one embodiment, the pharmaceutical composition of the invention comprises 3,5-diamino-6-(2,3-dichlorophenyl)-1,2,4-triazine and [2-Methoxy-5-(5-trifluoromethyl-tetrazol-1-yl)-benzyl]-(2S-phenyl-piperidin-3S-yl)-amine dihydrochloride.

In a further embodiment the pharmaceutical composition of the invention comprises 3,5-diamino-6-(2,3-dichlorophenyl)-1,2,4-triazine at subtherapeutic dose and [2-Methoxy-5-(5-trifluoromethyl-tetrazol-1-yl)-benzyl]-(2S-phenyl-piperidin-3S-yl)-amine dihydrochloride.

In another embodiment the pharmaceutical composition of the invention comprises 3,5-diamino-6-(2,3-dichlorophenyl)-1,2,4-triazine and [2-Methoxy-5-(5-trifluoromethyl-tetrazol-1-yl)-benzyl]-(2S-phenyl-piperidin-3S-yl)-amine dihydrochloride at subtherapeutic dose.

In one embodiment the pharmaceutical composition of the invention comprises R(−)-2,4-diamino-5-(2,3-dichlorophenyl)-6-fluoromethyl pyrimidine and [2-Methoxy-5-(5-trifluoromethyl-tetrazol-1-yl)-benzyl]-(2S-phenyl-piperidin-3S-yl)-amine dihydrochloride.

In another embodiment the pharmaceutical composition of the invention comprises R(−)-2,4-diamino-5-(2,3-dichlorophenyl)-6-fluoromethyl pyrimidine at subtherapeutic dose and [2-Methoxy-5-(5-trifluoromethyl-tetrazol-1-yl)-benzyl]-(2S-phenyl-piperidin-3S-yl)-amine dihydrochloride.

In a further embodiment, the pharmaceutical composition of the invention comprises R(−)-2,4-diamino-5-(2,3-dichlorophenyl)-6-fluoromethyl pyrimidine and [2-Methoxy-5-(5-trifluoromethyl-tetrazol-1-yl)-benzyl]-(2S-phenyl-piperidin-3S-yl)-amine dihydrochloride, at subtherapeutic dose.

In one embodiment, a method of treating a human or animal subject suffering from epilepsy, mood disorders or pain, is provided, which comprises administering to said subject an effective amount of any one of the pharmaceutical compositions above described.

In another embodiment, any one of the pharmaceutical compositions above described is provided for use in therapy.

In a further embodiment, any one of the pharmaceutical compositions above described is provided for use in the treatment of epilepsy, mood disorders or pain.

In an additional embodiment, the use of any one of the pharmaceutical compositions above described is provided for the treatment of epilepsy, mood disorders or pain.

The pharmaceutically acceptable salts of the NK1 receptor antagonist [2-Methoxy-5-(5-trifluoromethyl-tetrazol-1-yl)-benzyl]-(2S-phenyl-piperidin-3S-yl)-amine or of a Sodium Channel blocker which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, isethionate, citrate, tartrate, gluconate, camsylate, methanesulfonate, ethanesulfonate, benzenesulfonate, p-toluenesulfonate and palmoate salts. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutical compositions comprising pharmaceutically acceptable solvates of the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, or of a Sodium Channel blocker are within the scope of the invention.

The adjunctive therapy of the present invention is carried out by administering the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, together with a Sodium Channel Blocker, in any manner which provides effective levels of the compounds in the body at the same time. It will be appreciated that the compounds of the composition may be administered simultaneously, either in the same or separate dosage forms, or sequentially. It will also be understood that the compounds of the composition, whether presented simultaneously or sequentially, may be administered individually, or in multiples, or in any combination thereof.

The amount of a pharmaceutical composition according to the invention required to be effective as a treatment for mood disorders, psychotic disorders, epilepsy or pain may, of course, vary and is ultimately at the discretion of the medical practitioner. The factors to be considered include the route of administration and nature of the formulation, the subject mammal's body weight, age and general condition and the nature and severity of the condition to be treated.

Unless otherwise indicated, all weights of active ingredients are calculated in terms of the drug per se. The desired dose may preferably be presented as one, two, three, four, five, six or more sub-doses administered at appropriate intervals throughout the day.

A pharmaceutical composition of the invention as hereinabove defined for use in the treatment of mood disorders, psychotic disorders, epilepsy or pain may conveniently be presented as a pharmaceutical composition in a unitary dosage form. Thus pharmaceutical compositions incorporating both compounds are important embodiments of the present invention. Such compositions may take any physical form which is pharmaceutically acceptable, for example orally usable pharmaceutical compositions. Such adjunctive pharmaceutical compositions contain an effective amount of each of the compounds, which effective amount is related to the daily dose of the compounds to be administered. Each adjunctive dosage unit may contain the daily doses of all compounds, or may contain a fraction of the daily doses, such as one-third of the doses. Alternatively, each dosage unit may contain the entire dose of one of the compounds, and a fraction of the dose of the other compounds. In such case, the patient would daily take one of the combination dosage units, and one or more units containing only the other compound. The amounts of each drug to be contained in each dosage unit may depend on the identity of the drugs chosen for the therapy.

Pharmaceutical compositions of the invention as hereinabove defined for use in the treatment of mood disorders, psychotic disorders, epilepsy or pain include those suitable for oral, rectal, nasal, topical (including transdermal, buccal and sublingual), vaginal or parenteral (including subcutaneous, intramuscular, intravenous and intradermal) administration. The compositions may conveniently be presented in unit dosage form and may be prepared by any methods well known in the art of pharmacy. Such methods represent a further feature of the present invention and include the step of bringing into association the active ingredients with the carrier which constitutes one or more accessory ingredients. In general, the compositions are prepared by uniformly and intimately bringing into association the active ingredients with liquid carriers or finely divided solid carriers or both, and then if necessary shaping the product.

Pharmaceutical compositions of the present invention suitable for oral administration may be presented as discrete units such as capsules, caplets, cachets or tablets each comprising a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, sodium croscarmellose cross-linked povidone, cross-linked sodium carboxymethyl cellulose) surface-active or dispersing agent. Moulded tablets may be made by moulding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredients in an inert basis such as gelatin and glycerin, or sucrose and acacia; and mouthwashes comprising the active ingredients in a suitable liquid carrier. Compositions for rectal administration may be presented as a suppository with a suitable base comprising, for example, cocoa butter or polyethylene glycols.

Topical administration may also be by means of a transdermal iontophoretic device.

Pharmaceutical compositions suitable for vaginal administration may be presented as tablets, pessaries, tampons, creams, gels, pastes, foams or spray compositions comprising in addition to the active ingredients such carriers as are known in the art to be appropriate.

Pharmaceutical compositions suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, preservatives and solutes which render the formulation isotonic with the blood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injection, immediately prior to use.

Extemporaneous injection solutions and suspensions may be prepared from sterile powders, granules and tablets of the kind previously described.

It should be understood that in addition to the ingredients particularly mentioned above the compositions of this invention may include other agents conventional in the art having regard to the type of formulation in question, for example, those suitable for oral administration may include such further agents as sweeteners, thickeners and flavoring agents.

The pharmaceutical compositions of the invention comprising the two active ingredients may be prepared according to conventional techniques well known in the pharmaceutical industry. Thus, for example 3,5-diamino-6-(2,3-dichlorophenyl)-1,2,4-triazine and [2-Methoxy-5-(5-trifluoromethyl-tetrazol-1-yl)-benzyl]-(2S-phenyl-piperidin-3S-yl)-amine or pharmaceutically acceptable salts or solvates thereof, may be admixed together with suitable excipients such as those described above for the formulation of each of the active ingredients separately. Tablets may be prepared, for example by direct compression of such a mixture or using other conventional methods. Bilayer tablets may be prepared according to conventional procedure. Thus, for example, by separately compressing the two blends in a suitable tabletting machine with two filling stations. Capsules may be prepared by filling the blend along with suitable excipients into gelatin capsules, using a suitable filling machine. Controlled release forms for oral or rectal administration may be formulated in a conventional manner associated with controlled release forms.

Pharmaceutical compositions are often prescribed to the patient in "patient packs" containing the whole course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions and, therefore, lead generally to more successful treatment.

It will be understood that the administration of the pharmaceutical compositions of the invention by means of a single patient pack, or patient packs of each formulation, containing within a package insert instructing the patient to the correct use of the invention is a desirable additional feature of this invention.

According to a further aspect of the invention there is provided a multiple, for example, double or triple, pack comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt or solvate thereof, and a Sodium Channel blocker and an information insert containing directions on the use of the compositions of the invention.

EXPERIMENTAL DATA

The following table lists the used abbreviations:

| | |
|---|---|
| DMSO | dimethylsulfoxide |
| DCM | dichloromethane |
| DMAP | dimethylaminopyridine |
| DMF | dimethylformamide |
| TFA | Trifluoroacetic acid |
| LiHMDS | lithium bis(trimethylsilyl)amide |

-continued

| | |
|---|---|
| MeOH | Methanol |
| TEA | triethylamine |
| THF | tetrahydrofuran |
| MTBE | Methyl-t-butyl-ether |
| EtOAc, EA, AcOEt | Ethyl Acetate |
| CH | cyclohexane |
| Et$_2$O | Diethyl ether |
| EtOH | ethanol |
| DIPEA | Diisopropylethyl amine |
| BOC2O | di-t-butyl-dicarbonate |

Intermediate 1

[2S]-Phenyl-piperidin-[3S]-ylamine

[2S]-Phenyl-piperidin-[3S]-ylamine [2S,3S]-bis(4-methyl-benzoyloxy)-succinic acid salt (1:1) (6.9 g) was taken up in concentrated 0.880 aqueous ammonia solution (100 ml) and shaken for a few minutes. The basic solution was extracted with chloroform (3×150 ml), dried (Na$_2$SO$_4$), and concentrated in vacuo to give [2S]-phenyl-piperidin-[3S]-ylamine (1.85 g) as a colourless oil.

[α]$^{20}$D (HCl salt)=+65.480 (C=0.006 g/ml) $^1$H NMR (HCl salt, D$_2$O) δ 2.05 (m, 2H), 2.30 (m, 2H), 3.36 (m, 1H), 3.74 (m, 1H), 4.16 (q, 1H, J=4 Hz), 4.99 (d, 1H, J=4 Hz), 7.45 (m, 2H), 7.59 (m, 3H).

A small sample of the free base (50 mg) was derivatized as its trifluoroacetyl analogue for chiral HPLC analysis. The sample was dissolved in acetonitrile (4 ml) and treated with 1-(trifluoroacetyl)imidazole (0.4 ml). The solution was stirred at 650 for 1 h, concentrated in vacuo and the residue dissolved in dichloromethane (5 ml). The organic layer was washed with dilute sulphuric acid (2 ml), then the organic layer concentrated and dissolved in hexane-isopropylalcohol (98:2) for injection onto the HPLC column. Chiral HPLC (Chiracel-OD-H column, lot no. 09-02-20709, eluent hexane-isopropylalcohol 98:2, flow rate 1 ml/min, detection uv 230 nm, temperature 400) retention time 12.93 mins.

Intermediate 2

2-Hydroxy-5-tetrazol-1-yl-benzaldehyde

A solution of 4-tetrazol-1-yl-phenol (0.01 mol) in trifluoroacetic acid (20 ml) and hexamethylenetetramine (0.04 mol) was heated at 70° for 18 h, cooled to room temperature and quenched with 2N solution of sulfuric acid (50 ml). The mixture was extracted with ethyl acetate (3×100 ml), dried (MgSO$_4$), filtered and concentrated to give a residue which was purified by FCC (dichloromethane/methanol (9:1)) to afford the title compound in 30% yield.

T.l.c. (dichlormethane/methanol (9:1)) Rf 0.6

Intermediate 3 was prepared through a similar procedure to that described for Intermediate 2:

Intermediate 3

2-Hydroxy-5-(5-trifluoromethyl-tetrazol-1-yl)-benzaldehyde

From 4-(5-trifluoromethyl-tetrazol-1-yl)-phenol (45 mmol) to give the title compound (8.8 g) as a pale yellow solid.

T.l.c. (Hexane/ether (2:1)) Rf 0.36

Intermediate 4

2-Methoxy-5-tetrazol-1-yl-benzaldehyde

To a solution of 2-hydroxy-5-tetrazol-1-yl-benzaldehyde (2.63 mmol) in dimethylformamide (5 ml) was added potassium carbonate (3.95 mmol) and iodomethane (3.95 mmol) and the mixture was stirred under nitrogen atmosphere for 2 h. The mixture was poured into water (100 ml) and the white solid formed filtered to afford the title compound in a 67% yield.

T.l.c. (ether) Rf 0.45

Intermediate 5 was prepared through a similar procedure to that described for Intermediate 4:

Intermediate 5

2-Methoxy-5-(5-trifluoromethyl-tetrazol-1-yl)-benzaldehyde

From 2-hydroxy-5-(5-trifluoromethyl-tetrazol-1-yl)-benzaldehyde (1.56 mmol) to give the title compound as a yellow solid (0.48 g).

T.l.c. (ether/hexane (2:1)) Rf 0.38.

Representative NK1 Antagonist Example 6 (ENK6)

[2-Methoxy-5-(5-trifluoromethyl-tetrazol-1-yl)-benzyl]-([2S,3S]-2-phenyl-piperidin-3-yl)-amine dihydrochloride A mixture of [2S]-phenyl-piperidin-[3S]-ylamine (1.14 mmol), 2-methoxy-5-(5-trifluoromethyl-tetrazol-1-yl-benzaldehyde (1.2 mmol), sodium triacetoxyborohydride (2.37 mmol) and acetic acid (3 drops) in dichloromethane (25 ml) was stirred at 230 under nitrogen for 64 h. 2N sodium carbonate solution (50 ml) was added and the mixture extracted with dichloromethane (3×25 ml). The combined extracts were washed with saturated brine (50 ml), dried (MgSO$_4$) and evaporated. Purification by FCC with dichloromethane/ethanol/ammonia (400:10:1→100:10:1) gave a colourless viscous oil. This was dissolved in methanol (10 ml) and treated with 2N ethereal hydrogen chloride (~10 ml). Evaporation in vacuo and trituration with i-propyl acetate gave the title compound as a white solid (210 mg).

T.l.c. (Dichloromethane/ethanol/ammonia (200:10:1)) Rf 0.39 Optical Rotation (c 0.003 g/ml. water)+50.35°.

Representative Na Channel Blocker Example 7 (ENa7)

3,5-diamino-6-(2,3-dichlorophenyl)-1,2,4-triazine

Lamotrigine, 3,5-diamino-6-(2,3-dichlorophenyl)-1,2,4-triazine is disclosed in U.S. Pat. No. 4,602,017 and EP0021121. Products comprising lamotrigine are marketed under the trade name LAMICTAL™ by the GlaxoSmithKline group of companies.

Intermediate 6

1-(1,1-dimethylethyl)2-methyl(2S)-5-oxo-1,2-pyrrolidinedicarboxylate

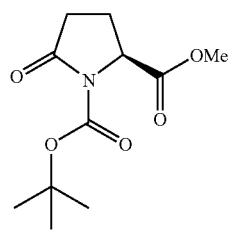

To a solution of commercially available methyl 5-oxo-L-prolinate (20 g, 140 mmol) in DCM (200 ml) were added triethylamine (19.6 ml, 140 mmol), DMAP (17.2 g, 140 mmol) and then dropwise a solution of BOC$_2$O (61 g, 280 mmol) in DCM (100 ml). The resulting red mixture was stirred at room temperature for 2 hours. Then the solvent was removed under reduced pressure and the crude material was purified by chromatography on silica gel eluting with cyclohexane/ethyl acetate (7:3 to 4:6) to afford (after a trituration in hexane/diethylether 1:1) the title compound as a white solid (32.4 g, 96%); R$_f$ (cyclohexanes:ethyl acetate=65:35): 0.21; $^1$H NMR (300 MHz, CDCl$_3$) δ(ppm): 4.62 (dd, 1H), 3.78 (s, 3H), 2.68-2.58 (m, 1H), 2.52-2.45 (m, 1H), 2.37-2.27 (m, 1H), 2.08-1.97 (m, 1H), 1.48 (s, 9H).

Intermediate 7 methyl(2S)-2-({[(1,1-dimethylethyl)oxy]carbonyl}amino)-5-oxo-5-{4-[(phenylmethyl)oxy]phenyl}pentanoate

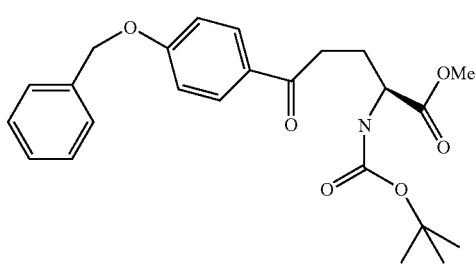

n-Butyl lithium 1.6M solution in hexanes (0.88 ml, 1.4 mmol) was added dropwise to a solution of commercially available 1-bromo-4-[(phenylmethyl)oxy]benzene (390 mg, 1.48 mmol) in dry THF (2 ml) at −78° C. under nitrogen atmosphere. The resulting suspension was stirred at −78° C. for 40 minutes and then it was added dropwise to a solution of 1-(1,1-dimethylethyl)2-methyl(2S)-5-oxo-1,2-pyrrolidinedicarboxylate (300 mg, 1.23 mmol) in dry THF (2.4 ml) previously cooled to −78° C. The mixture was stirred at −78° C. for 40 minutes and at −40° C. for 1 h, then it was quenched at −40° C. with an aqueous saturated ammonium chloride solution. The mixture was diluted with water and extracted with ethyl acetate. The organic phase was then washed with brine, dried over Na$_2$SO$_4$, and evaporated under reduced pressure to give the crude material, which was purified by chromatography on silica gel eluting with cyclohexane/ethylacetate (95:5), thus affording the title compound as a white solid (170 mg, 32%); R$_f$ (cyclohexane:ethyl acetate=8:2): 0.30; $^1$HNMR (300 MHz, CDCl$_3$) δ(ppm): 7.95 (d, 2H), 7.50-7.33 (m, 5H), 7.03 (d, 2H), 5.20 (bs, 1H), 5.15 (s, 2H), 4.45-4.35 (m, 1H), 3.78 (s, 3H), 3.15-2.95 (m, 2H), 2.36-2.26 (m, 1H), 2.16-2.02 (m, 1H), 1.45 (s, 9H).

Intermediate 8 methyl(2S)-5-{4-[(phenylmethyl)oxy]phenyl}-3,4-dihydro-2H-pyrrole-2-carboxylate

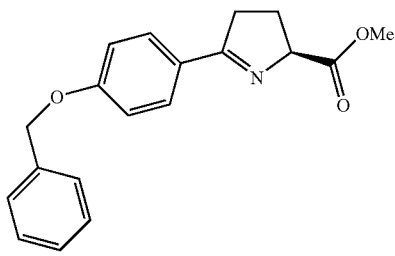

To a solution of methyl(2S)-2-({[(1,1-dimethylethyl)oxy]carbonyl}amino)-5-oxo-5-{4-[(phenylmethyl)oxy]phenyl}pentanoate (323 mg, 0.75 mmol) in dry DCM (4 ml) at 0° C., under nitrogen atmosphere was added trifluoroacetic acid (1 ml) dropwise. The resulting pale pink solution was allowed to warm to room temperature over 1 hour, then it was evaporated under reduced pressure, affording the title compound (D7, 291 mg, 0.68 mmol, 91%) as a greenish oil which may be used in the next step without any further purification; R$_t$ (HPLC): 3.69 min; MS: (ES/+) m/z: 310 [MH$^+$], C19H19NO3 requires 309.

Intermediate 9 methyl(5R)-5-{4-[(phenylmethyl)oxy]phenyl}-L-prolinate

Intermediate 10 methyl(5S)-5-{4-[(phenylmethyl)oxy]phenyl}-L-prolinate

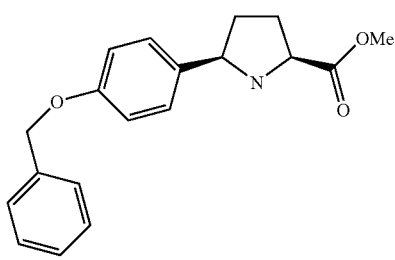

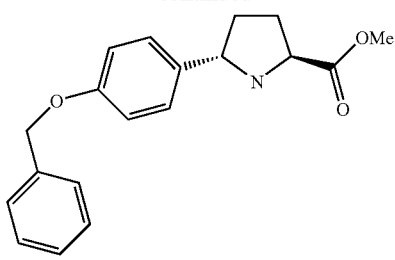

To a solution of methyl(2S)-5-{4-[(phenylmethyl)oxy]phenyl}-3,4-dihydro-2H-pyrrole-2-carboxylate (13.7 g, 32.4 mmol) in MeOH (200 ml) was added PtO₂ (240 mg) and the mixture was stirred under a hydrogen atmosphere (2 atmos) for 6 hours. Then the catalyst was filtered off and the solvent removed under reduced pressure to give a red oil which was dissolved in ethyl acetate and washed with NaHCO₃ solution. The resulting crude material was purified by chromatography on silica gel eluting with cyclohexane/ethyl acetate (9:1 to 8:2) to afford the title compounds:

Intermediate 9, 4.15 g, 13.3 mmol, Y=41%. MS: (ES/+) m/z: 312 [MH⁺]. C19H21NO3 requires 311. Rt (HPLC): 3.80 min. Rf (cyclohexane:ethyl acetate=7:3): 0.18. ¹HNMR (300 MHz, CDCl₃) δ(ppm): 7.40 (d, 2H); 7.35 (t, 2H); 7.33 (d, 2H); 7.29 (t, 1H); 6.93 (d, 2H); 5.03 (s, 2H); 4.23 (dd, 1H); 4.00 (dd, 1H); 3.71-3.79 (m, 3H); 2.18-2.30 (m, 1H); 2.09-2.18 (m, 2H); 1.67-1.78 (m, 1H). NOE between the proton at C2 and the proton at C5 could be observed.

Intermediate 10, 0.6 g, 1.9 mmol, Y=6%. MS: (ES/+) m/z: 312 [MH⁺]. C19H21NO3 requires 311; Rt (HPLC): 3.73 min. Rf (cyclohexane:ethyl acetate=7:3): 0.32. ¹HNMR (300 MHz, CDCl₃) δ(ppm): 7.40 (d, 2H); 7.35 (t, 2H); 7.29 (d, 2H); 7.28 (t, 1H); 6.91 (d, 2H); 4.97-5.07 (m, 2H); 4.29 (dd, 1H); 4.09 (dd, 1H); 3.71-3.75 (m, 3H); 2.29-2.42 (m, 1H); 2.09-2.20 (m, 1H); 1.90-2.02 (m, 1H); 1.69-1.82 (m, 1H). NOE between the proton at C2 and the proton at C5 was not observed.

Intermediate 11

(5R)-5-{4-[(phenylmethyl)oxy]phenyl}-L-proline

Intermediate 12

(5R)-1-{[(1,1-dimethylethyl)oxy]carbonyl}-5-{4-[(phenylmethyl)oxy]phenyl}-L-proline

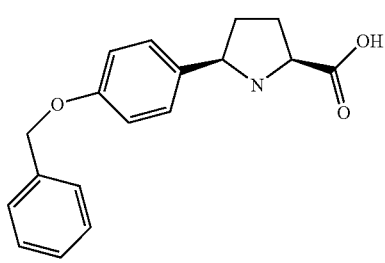

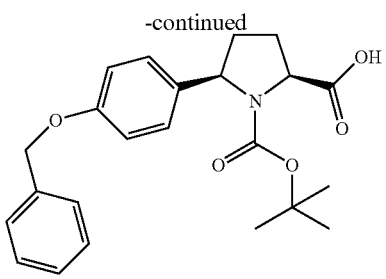

To a solution of methyl(5R)-5-{4-[(phenylmethyl)oxy]phenyl}-L-prolinate (120 mg, 0.38 mmol) in THF (2.3 ml) was added LiOH monohydrate (26 mg, 0.61 mmol) dissolved in water (1.1 ml), followed by methanol (1.1 ml). The resulting solution was stirred at room temperature for 2.5 hours, then left overnight at −18° C. Then the organic solvent was evaporated under reduced pressure maintaining the temperature at 38° C. and the aqueous residue containing the acid intermediate (Rt (HPLC)=3.63 min. MS: (ES/+) m/z: 298 [MH⁺]. C18H19NO3 requires 297) was treated with BOC₂O (168 mg, 0.77 mmol) dissolved in THF (1.1 ml). The reaction mixture was stirred at room temperature for 3.5 hours. The organic solvent was evaporated and the basic aqueous solution was acidified at 0° C. with aqueous 1N HCl solution to pH=3, this acidic aqueous solution was extracted with ethyl acetate (2×10 ml). The organic phase dried over Na₂SO₄ and evaporated under reduced pressure gave a solid, which was titurated in n-hexanes (3×6 ml) affording the title compound as a white powder (137 mg, 90% for two steps); Rt (HPLC): 5.81 min; Rf (cyclohexane:ethyl acetate=1:1): 0.34; MS: (ES/+) m/z: 420 [M+Na⁺]C23H27NO5 requires 397; MS: (ES/−) m/z: 396 [M−H]C23H27NO5 requires 397; ¹H NMR (300 MHz, CDCl₃) δ(ppm): 7.5-7.3 (m, 5H), 7.10 (bm, 2H), 6.90 (d, 2H), 5.08 (s, 2H), 4.65 (bm, 1H), 4.50 (bm, 1H), 2.58 (bm, 1H), 2.31 (bm, 1H), 2.11-1.90 (m, 2H), 1.16 (s, 9H).

Intermediate 13

1,1-dimethylethyl(2S,5R)-2-(aminocarbonyl)-5-{4-[(phenylmethyl)oxy]phenyl}-1-pyrrolidinecarboxylate

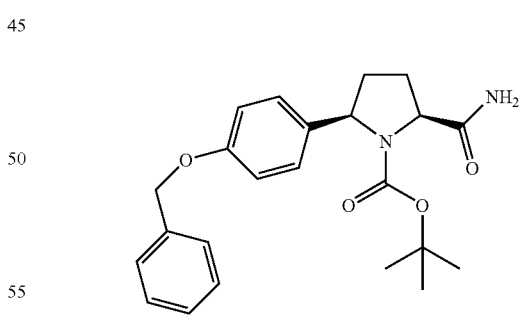

To a solution of (5R)-1-{[(1,1-dimethylethyl)oxy]carbonyl}-5-{4-[(phenylmethyl)oxy]phenyl}-L-proline (1.44 g, 3.62 mmol) in dry DMF (20 ml) were added DIPEA (1.26 ml, 7.24 mmol), then TBTU (1.23 g, 3.98 mmol) and after 20 minutes, 1,1,1,3,3,3-hexamethyldisilazane (1.15 ml, 5.43 mmol). The reaction mixture was stirred at room temperature for 2 h, then it was treated with aqueous 5% NaHCO₃ solution (30 ml) and stirred for further 30 minutes. The resulting mixture was diluted with water and extracted with ethyl acetate. The organic phase was then washed twice with brine/ ice, dried over Na$_2$SO$_4$ and evaporated to give a colourless oil. This crude material was purified by chromatography on silica gel eluting with cyclohexane/ethyl acetate (7:3 to 5:5) to afford the title compound (1.25 g, 87%); R$_t$ (HPLC): 5.51 min; R$_f$ (cyclohexane:ethyl acetate=1:1): 0.29. MS: (ES/+) m/z: 419 [M+Na$^+$]; C23H28N2O4 requires 396.

Intermediate 14

1,1-dimethylethyl(2S,5R)-2-(aminocarbonyl)-5-(4-hydroxyphenyl)-1-pyrrolidinecarboxylate

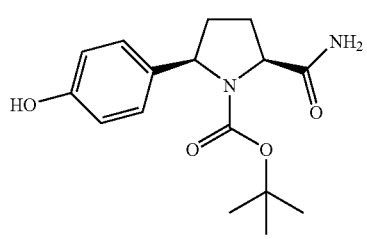

To a solution of 1,1-dimethylethyl(2S,5R)-2-(aminocarbonyl)-5-{4-[(phenylmethyl)oxy]phenyl}-1-pyrrolidinecarboxylate (1.2 g, 3.02 mmol) in methanol (25 ml) was added Pd/C 10% wt (210 mg) and the mixture was stirred under hydrogen (1 atm) for 6 hours. The catalyst was filtered off and the solvent removed under reduced pressure to give the title compound as a white solid (870 mg, 94%); R$_t$ (HPLC): 3.61 min; R$_f$ (cyclohexane:ethyl acetate=1:1): 0.18; MS: (ES/+) m/z: 329 [M+Na$^+$]. C16H22N2O4 requires 306; $^1$H NMR (300 MHz, d$_6$-DMSO) δ ppm: 9.15 (bs, 1H); 7.40 (bm, 2H); 7.30 (s, 1H); 6.90 (s, 1H); 6.65 (d, 2H); 4.50-4.80 (m, 1H); 4.05-4.28 (m, 1H); 2.07-2.24 (m, 1H); 1.95-2.07 (m, 1H); 1.60-1.89 (m, 2H); 1.00-1.45 (m, 9H).

Intermediate 15

1,1-dimethylethyl(2S,5R)-2-(aminocarbonyl)-5-(4-{[(2-fluorophenyl)methyl]oxy}phenyl)-1-pyrrolidinecarboxylate

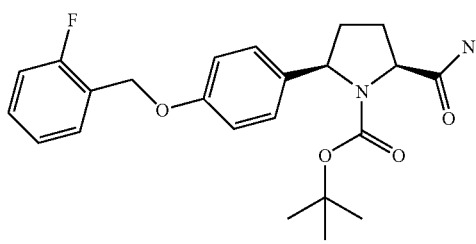

1-(Bromomethyl)-2-fluorobenzene (30 μl, 0.220 mmol) was added to a solution of 1,1-dimethylethyl(2S,5R)-2-(aminocarbonyl)-5-(4-hydroxyphenyl)-1-pyrrolidinecarboxylate (45 mg, 0.146 mmol) and potassium carbonate (30 mg, 0.217 mmol) in acetonitrile (2 ml). The mixture was stirred overnight at room temperature. After the reaction was finished, as shown by TLC, ethyl acetate and water were added. The organic phase was then washed with brine, dried (Na$_2$SO$_4$), filtered and evaporated. The crude material was purified by chromatography on silica gel using cyclohexane/ethyl acetate (7:3 to 6:4) to afford the title compound (51 mg, 85%); Rt (HPLC): 5.56 min; Rf (cyclohexane:ethyl acetate=1:1): 0.28; $^1$H NMR (300 MHz, CDCl$_3$) δ(ppm): 7.56-7.48 (m, 1H); 7.37-7.28 (m, 1H); 7.24-7.06 (m, 5H); 6.93 (d, 2H); 5.45-5.37 (br. s, 1H); 5.15 (s, 2H); 4.73-4.60 (m, 1H); 4.53-4.45 (m, 1H); 2.58-2.48 (m, 1H); 2.34-2.25 (m, 1H); 2.09-1.93 (m, 2H); 1.28-1.13 (br. s, 9H).

Intermediate 16

1-[(4-bromophenoxy)methyl]-2-fluorobenzene

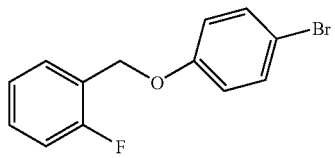

Procedure 1: To a solution of 4-bromophenol (502.08 g) dissolved in acetone (7322 mL) was added K$_2$CO$_3$ (570 g) and then benzylbromide (523 g). The mixture was heated under reflux for 2 hrs. The reaction mixture was then cooled at 25° C., filtered and the filter cake was washed with MTBE (1046 mL). The combined filtrate was concentrated to 1000 mL and MTBE (4184 mL) were added. The mixture was washed with an aqueous 1M NaOH solution (1464 mL), then with brine (1300 mL) and the organic phase was concentrated to dryness. THF (1300 mL) was added and the solvent was removed under reduced pressure to afford the title compound (902.1 g); $^1$H NMR (400 MHz, DMSO-d6) δ(ppm): 7.54 (td, 1H); 7.46 (d, 2H); 7.42 (m, 1H); 7.23 (m, 2H); 7.01 (d, 2H); 5.13 (s, 2H).

Procedure 2: A stirred mixture of 4-bromophenol (19.22 g, 111 mmol), orthofluorobenzyl bromide (20 g, 105.8 mmol) and potassium carbonate (21.9 g, 158.4 mmol) in acetone (280 ml) was heated at reflux for 6 hours. The reaction mixture was cooled to room temperature and filtered, washing the solid with TBME (40 ml). The combined filtrate and washings were concentrated under vacuum to a final volume of about 40 ml. The resulting solution was diluted with TBME (160 ml) and washed with 1M sodium hydroxide and brine, then concentrated under vacuum to an oil which slowly solidified to give the title compound (28.9 g).

1H NMR (300 MHz, CHCl3-d). δ(ppm): 5.10 (s, 2H), 6.86 (m, 2H), 7.10 (m, 1H), 7.17 (m, 1H), 7.29 (m, 1H), 7.35 (m, 2H), 7.38 (m, 1H).

Intermediate 17 methyl(2S)-2-({[(1,1-dimethylethyl)oxy]carbonyl}amino)-5-(4-{[(2-fluorophenyl)methyl]oxy}phenyl)-5-oxopentanoate

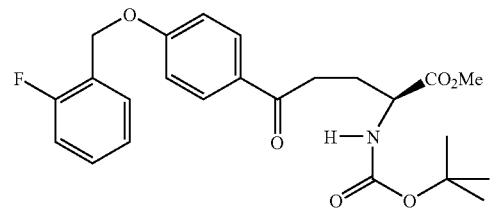

Procedure 1: To a stirred suspension of magnesium metal (90 g) in dry THF (600 mL) under a nitrogen atmosphere at room temperature was added iodine (0.3 g). The mixture was heated to an internal temperature of 64+/−2° C. A solution of 1-[(4-bromophenoxy)methyl]-2-fluorobenzene (693 g) in THF (1500 mL) was added in two batches. Firstly 45 mL was added. Secondly, the remaining solution (1455 mL) was added dropwise. After addition, the reaction was heated at reflux for 1 h. The reaction mixture was cooled to room temperature. This reaction mixture was then added slowly to a solution of commercially available 1-tert-butyl 2-methyl (2S)-5-oxopyrrolidine-1,2-dicarboxylate (300 g) in THF (1500 mL) cooled to −60° C., maintaining the internal temperature below −60° C. The addition was completed in 2 hours. The reaction mixture was stirred for a further 15 minutes after addition. Isopropyl alcohol (300 mL) was then added dropwise whilst maintaining the temperature below −60° C. A mixture of aqueous saturated ammonium chloride solution/aqueous saturated sodium chloride solution (2/1; 900 mL) was added whilst maintaining the temperature at −50° C. Water (600 mL) was added to dissolve the yellow precipitate. The organic phase was separated and was washed with aqueous 13% NaCl solution (600 mL). The organic phase was concentrated to dryness. EtOAc (1500 mL) was then added and the solution was evaporated under reduced pressure to remove water. The residue was purified by chromatography on silica gel eluting with cyclohexane/ethyl acetate (90:10 to 8:2) to afford the title compound (287 g); $^1$H NMR (600 MHz, DMSO-d6) δ(ppm): 7.93 (d, 2H); 7.57 (td, 1H); 7.44 (m, 1H); 7.27 (m, 3H); 7.14 (d, 2H); 5.24 (s, 2H); 4.04 (m, 1H); 3.61 (s, 3H); 3.03 (m, 2H); 1.94 (m, 2H); 1.38 (s, 9H).

Procedure 2: To a mixture of magnesium turnings (12.79 g. 533 mol), a trace of iodine and 1,2-dibromoethane in THF (86 ml) at 70-75° C., a solution of (4-bromophenyl (2-fluorophenyl)methyl ether) (100 g, 355.6 mmol) in THF (216.25 ml) was added over about 2 hours. The mixture was heated for a further 2 hours at 70-75° C. then cooled to room temperature to give a solution of the Grignard reagent. A solution of 1-(1,1-dimethylethyl)2-methyl(2S)-5-oxo-1,2-pyrrolidinedicarboxylate (43.25 g, 177.8 mmol) in THF (216.25 ml) was cooled to −60° C. and the solution of the Grignard reagent was added over 1 hour, then the mixture was stirred for 3 hours at −60° C. Isopropanol (43.25 ml) was added dropwise, followed by saturated aqueous ammonium chloride (86.5 ml) and brine (43.25 ml), then the mixture warmed to room temperature. Water (173 ml) and 50% acetic acid (50 ml) to pH 6-7, followed by ethyl acetate (129.7 ml). The layers were separated and the aqueous extracted with ethyl acetate (2×129.7 ml). The combined organic layers were washed with brine then concentrated under vacuum. The residue was stirred with hexane (216.2 ml), then the solid was filtered and washed with hexane. To the resulting solid, isopropanol (432.5 ml) was added and the mixture stirred at 45° C. for 15 minutes, then cooled to 5-10° C. and stirred for 2 hours. The solid was filtered, washed with isopropanol and dried to give the title compound as a solid.

1H NMR (300 MHz, CHCl3-d): δ(ppm): 1.42 (s, 9H); 2.04 (m, 1H); 2.28 (m, 1H); 3.03 (m, 2H); 3.74 (s, 3H); 4.37 (m, 1H); 5.19 (b, 1H); 5.20 (s, 2H); 7.02 (d, 2H); 7.11 (t, 1H); 7.17 (t, 1H); 7.33 (m, 1H); 7.48 (t, 1H); 7.94 (d, 2H).

Intermediate 18 methyl(2S)-5-{4-[(2-fluorobenzyl)oxy]phenyl}-3,4-dihydro-2H-pyrrole-2-carboxylate

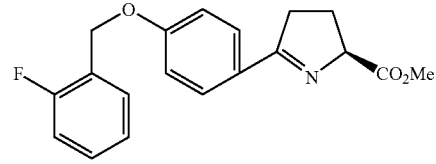

Procedure 1: To a solution of methyl(2S)-2-({[(1,1-dimethylethyl)oxy]carbonyl}amino)-5-(4-{[(2-fluorophenyl)methyl]oxy}phenyl)-5-oxopentanoate (243 g) in dry DCM (2430 mL) at 0° C. was added TFA (461 mL) dropwise. The mixture was allowed to warm to room temperature and stirred for 3 hrs. Solvent and the excess TFA were removed under vacuum and the resulting dark oil was stripped with EtOAc (2×1215 mL) and left overnight under a high vacuum. The title compound (392 g) was obtained as a red oil and used in the following step without any further purification; $^1$H NMR (400 MHz, DMSO-d6) δ(ppm): 8.16 (m, 2H); 7.60 (td, 1H); 7.46 (m, 1H); 7.34 (m, 2H); 7.27 (m, 2H); 5.32 (s, 2H); 5.25 (m, 1H); 3.77 (s, 3H); 3.57 (m, 2H); 2.60 (m, 1H); 2.34 (m, 1H).

Procedure 2: A solution of methyl(2S)-2-({[(1,1-dimethylethyl)oxy]carbonyl}amino)-5-(4-{[(2-fluorophenyl)methyl]oxy}phenyl)-5-oxopentanoate (46 g, 103 mmol) in DCM (437 ml) was treated dropwise with trifluoroacetic acid (87.4 ml) at 0-5° C., then warmed to room temperature and stirred for 3 hours. The solution was cooled to 0-5° C. and sodium hydroxide solution added to a final pH of about 7. The aqueous layer was separated and extracted with DCM (13 ml), then the combined organic layers were washed with water, dried over sodium sulphate, then concentrated under vacuum to give the title compound as a solid (33.3 g).

1H NMR (300 MHz, CHCl3-d): δ(ppm): 2.35 (m, 2H); 2.95 (m, 1H); 3.12 (m, 1H); 3.78 (s, 3H); 4.89 (dd, 1H); 5.18 (s, 2H); 7.00 (d, 2H); 7.10 (m, 1H); 7.16 (m, 1H); 7.29 (m, 1H); 7.5 (t, 1H); 7.85 (d, 2H).

Intermediate 19

Methyl(5R)-5-{4-[(2-fluorobenzyl)oxy]phenyl}-L-prolinate

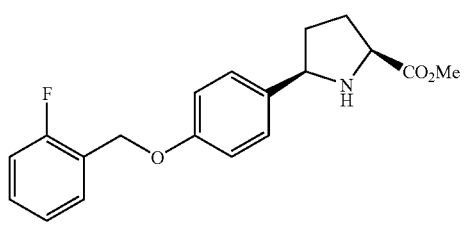

Procedure 1: Methyl(2S)-5-{4-[(2-fluorobenzyl)oxy]phenyl}-3,4-dihydro-2H-pyrrole-2-carboxylate (392 g) was dissolved in EtOAc (3160 mL) in a hydrogenation reactor. 5% platinum on carbon (Engelhard code 44379, moisture content ca. 50%, 15.8 g) was added, the reactor filled with hydrogen gas to a pressure of 2 atm and the reaction mixture was stirred for approximately 1.5 hours. The reactor was depressurised and the spent catalyst filtered through Celite, washing through with EtOAc (2×500 mL, then further 200 mL). Aqueous saturated NaHCO$_3$ solution (600 mL) was added to the filtrate, followed by aqueous 13% w/w Na$_2$CO$_3$ solution (up to pH=9, 1000 mL). The mixture was stirred for minutes and phases were then allowed to separate. The aqueous phase was removed and then the organic layer was washed once with brine (600 mL). The resulting solution was concentrated to dryness and the residue was purified by flash chromatography eluting with cyclohexane/ethyl acetate (1:1) to afford the title compound (133 g); $^1$H NMR (600 MHz, DMSO-d6) δ(ppm): 7.55 (dt, 1H); 7.41 (m, 1H); 7.34 (m, 2H); 7.23 (m, 2H); 6.97 (m, 2H); 5.12 (s, 2H); 4.09 (dd, 1H); 3.83 (dd, 1H); 3.66 (s, 3H); 2.97 (bs, 1H); 2.04 (m, 2H); 1.94 (m, 1H); 1.52 (m, 1H).

Procedure 2: A solution of methyl(2S)-5-(4-{[(2-fluorophenyl)methyl]oxy}phenyl)-3,4-dihydro-2H-pyrrole-2-carboxylate (34 g, 103.5 mmol) in ethyl acetate (272 ml) was placed in an autoclave and treated with trifluoroacetic acid (7.2 ml). 5% Platinum on carbon catalyst (1.7 g) was transferred as a slurry with ethyl acetate (68 ml) and the reaction was stirred at room temperature under 50 psi hydrogen pressure for 5 hours. The mixture was filtered through Hyflo, washing with ethyl acetate (272 ml), then the filtrate was washed with aq sodium carbonate solution and brine, dried over sodium sulphate, then concentrated under vacuum, and the residue dried to give the title compound as a crude oil (also comprising some of the anti isomer), 1H NMR (300 MHz, CHCl3-d): δ(ppm): 1.7 (m, 1H); 2.18 (m, 4H); 3.75 (s, 3H); 3.91 (m, 1H); 4.15 (m, 1H); 5.13 (s, 2H); 6.96 (d, 2H); 7.07 (m, 1H); 7.15 (m, 1H); 7.30 (m, 1H); 7.38 (d, 2H); 7.5 (t, 1H).

Representative Na Channel Blocker Example 8
(ENa8)

(5R)-5-(4-{[(2-Fluorophenyl)methyl]oxy}phenyl)-L-prolinamide

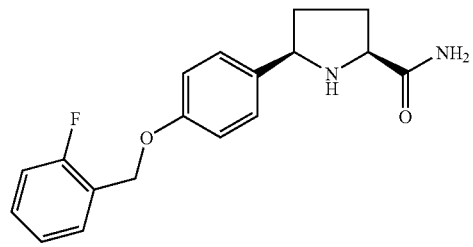

Procedure 1: A solution of methyl(5R)-5-(4-{[(2-fluorophenyl)methyl]oxy}phenyl)-L-prolinate (32.5 g, 98.6 mmol) in methanol (65 ml) was cooled to 0-10° C. A solution of ammonia in methanol (ca 11.2M) was added in four portions over 11 hours (175.4 ml, 43.8 ml, 43.8 ml. 43.8 ml) then the reaction stirred at 15-20° C. for 22 hours. Ammonia and methanol were removed under vacuum, then toluene (65 ml) was added and the mixture heated to 60-65° C. to give a solution, which was then concentrated under vacuum and the residue dried at 60° C. Toluene (130 ml) and methanol (0.32 ml) were added to the residue and the mixture heated to 70-75° C. The resulting solution was then cooled to 15-20° C. and stirred for 1 hour. The solid was filtered, washed with toluene and dried at 45-50° C. to give the title compound (21.8 g) as a solid.

$^1$H NMR (500 MHz, DMSO-d6) δ(ppm): 1.39 (m, 1H); 1.84 (m, 1H); 2.04 (m, 2H); 3.54 (m, 1H); 4.09 (m, 1H); 5.12 (s, 2H); 6.96 (d, 2H); 7.15 (m, 1H); 7.25 (m, 2H); 7.34 (d, 2H); 7.41 (m, 2H); 7.55 (t, 1H).

Procedure 2: Methyl(5R)-5-{4-[(2-fluorobenzyl)oxy]phenyl}-L-prolinate (127 g) was dissolved in 7N NH$_3$ solution in MeOH (1016 mL) and the mixture was stirred at room temperature for 24 hrs. Further 7N NH$_3$ solution in MeOH (63 mL) was added and the mixture stirred for a further 15 hours. The solvent was removed under reduced pressure and MeOH (635 mL) was added. The solution was evaporated to dryness and the white solid obtained was left under high vacuum over the weekend. The white solid was suspended in a mixture of MTBE/Toluene 1:1 (254 mL) at 20° C. and stirred for 1 hr. The suspension was filtered and the solid washed with MTBE (254 mL). The white solid was dried at 40° C. overnight under vacuum affording 122.4 g of material. This material was resuspended in a mixture of MTBE/toluene 1:1 (245 mL) and stirred at room temperature for 1 hour. The mixture was filtered and the solid was washed with MTBE (245 mL). The white solid obtained was dried at 40° C. overnight under vacuum to give the title compound (109 g). $^1$H NMR (600 MHz, DMSO-d6) δ(ppm): 7.54 (td, 1H); 7.41 (m, 1H); 7.38 (m, 2H); 7.34 (d, 2H); 7.24 (m, 2H); 7.13 (bs, 1H); 6.96 (d, 2H); 5.12 (s, 2H); 4.09 (dd, 1H); 3.55 (dd, 1H); 3.24 (bs, 1H); 2.07 (m, 1H); 2.00 (m, 1H); 1.85 (m, 1H); 1.40 (m, 1H).

Representative Na Channel Blocker Example 9
(ENa9)

(5R)-5-(4-{[(2-fluorophenyl)methyl]oxy}phenyl)-L-prolinamide hydrochloride

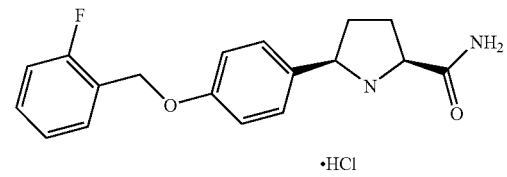

Procedure 1: To a solution of 1,1-dimethylethyl(2S,5R)-2-(aminocarbonyl)-5-(4-{[(2-fluorophenyl)methyl]oxy}phenyl)-1-pyrrolidinecarboxylate (51 mg, 0.123 mmol) in a mixture of ethyl acetate (0.9 ml) and methanol (1 ml) was added acetylchloride (28 μl, 2.5 eq) at 0° C. The mixture was shaken for 1.5 h and slowly allowed to warm to room temperature. After evaporating the solvent, the residue was triturated with diethyl ether to afford the title compound as a white solid (42 mg, quant.); Chiral HPLC: Column: chiralcel OD 10 um, 250×4.6 mm; Mobile phase: A: n-Hexane; B: Ethanol; Gradient: isocratic 30% B; Flow rate: 0.8 ml/min; UV wavelength range: 200-400 nm; Analysis time: 22 min; ret. time: 12.0 min. [α]$_D$=−30.5°. MS: (ES/+) m/z: 315 [MH$^+$], C18H19FN2O2 requires 314; $^1$H NMR (400 MHz, DMSO-d6) δ ppm 10.19 (br. s., 1H), 8.13 (br. s., 1H), 7.94 (s, 1H), 7.60-7.77 (m, 1H), 7.51 (dt, 1H), 7.43 (d, 2H), 7.34-7.41 (m, 1H), 7.23 (d, 1H), 7.18 (dd, 1H), 7.05 (d, 2H), 5.13 (s, 2H), 4.49-4.60 (m, 1H), 4.19-4.28 (m, 1H), 2.17-2.38 (m, 2H), 2.05-2.16 (m, 1H), 1.92-2.03 (m, 1H).

Procedure 2: ((5R)-5-(4-{[(2-fluorophenyl)methyl]oxy}phenyl)-L-prolinamide) (109 g) was dissolved in DCM (654 mL) and Et₂O (654 mL) was added at room temperature. HCl 1N in Et₂O (380.4 mL) was added dropwise at room temperature. The suspension was cooled to 0° C. and stirred at this temperature for 1 hr. The solid was filtered, washed with Et₂O (2×327 mL) and dried at 40° C. under vacuum overnight to afford Form 1 crystals of the title compound (121.24 g). ¹H NMR (600 MHz, DMSO-d6) δ(ppm): 10.72 (bs, 1H); 8.10 (bs, 1H); 8.08 (s, 1H); 7.72 (s, 1H); 7.56 (td, 1H); 7.49 (d, 2H); 7.43 (qd, 1H); 7.25 (m, 2H); 7.10 (d, 2H); 5.17 (s, 2H); 4.61 (dd, 1H); 4.30 (dd, 1H); 2.32 (m, 2H); 2.16 (m, 1H); 2.02 (m, 1H).

Procedure 3: ((5R)-5-(4-{[(2-fluorophenyl)methyl]oxy}phenyl)-L-prolinamide) (10 g, 31.8 mmol) was dissolved in DCM (50 ml) and stirred with charcoal (1 g), then filtered, washing with DCM (30 ml). The residue was concentrated under vacuum, removing about 20 ml of DCM. Ether (60 ml) was added, followed by a solution of HCl in ether (0.84N, 40 ml), and the mixture was then stirred at 20-25° C. for 30 min, then cooled to 0-5° C. and stirred for 2 hours. The solid was filtered, washed with ether, then dried at room temperature to give Form 1 crystals of title compound (10.25 g).

¹H NMR (300 MHz, DMSO-d₆) δ (ppm): 2.04 (m, 1H); 2.18 (m, 1H); 2.32 (m, 2H); 4.34 (m, 1H); 4.64 (m, 1H); 5.18 (s, 2H); 7.10 (d, 2H); 7.25 (m, 2H); 7.40-7.60 (m, 4H); 7.77 (s, 1H); 8.24 (s, 1H); 11.03 (b, 1H).

Procedure 4: In a round bottom flask, a solution of ((5R)-5-(4-{[(2-fluorophenyl)methyl]oxy}phenyl)-L-prolinamide) (1.4 g, 4.45 mmol) in ethylacetate (14 ml) and MeOH (2.5 ml) at 0° C. was treated with HCl 1M in diethylether (1.1 eq, 4.89 ml). The precipitation occurred quite soon and the mixture was stirred at 0° C. for 1 h. The mixture was then diluted with dry diethylether (10 ml) and then filtered on a Gooch filter (porosity 4, diameter 5 cm). The cake was washed on the filter with dry diethylether (2×20 ml) and the white solid thus obtained was transferred into a round bottom flask, dried under high vacuum at 40° C. for 2 h and then at room temperature for 18 hours. A white solid was obtained (1.51 g) of Form 1 crystals of the title compound.

Procedure 5: ((5R)-5-(4-{[(2-fluorophenyl)methyl]oxy}phenyl)-L-prolinamide) (25 g, 79.5 mmol) was dissolved in ethyl acetate (750 ml) and stirred with charcoal (2.5 g), then filtered, washing with ethyl acetate (125 ml). To the filtrate and washings, a solution of HCl in ether (1N, 103 ml), was added over 30 minutes at 20-25° C. and the mixture was then stirred at 20-25° C. for 30 min, then cooled to 0-5° C. and stirred for 2 hours. The solid was filtered, washed with ethyl acetate (2×70 ml), then dried at room temperature to give Form 1 crystals of the title compound. (25.5 g).

Unique and discriminating peaks of Form 1 of the title compound of Example 9 have been identified and are illustrated in the table below:

| Position [°2Th.] | d-spacing [Å] |
|---|---|
| 4.7 | 18.6 |
| 9.5 | 9.3 |
| 12.6 | 7.0 |
| 14.3 | 6.2 |
| 19.2 | 4.6 |
| 20.3 | 4.4 |
| 20.9 | 4.2 |
| 24.0 | 3.7 |
| 26.4 | 3.4 |

Melting point: 230° C.

Representative Na Channel blocker Example 10 (ENa10)

(5R)-5-(4-{[(2-fluorophenyl)methyl]oxy}phenyl)-L-prolinamide methanesulfonate

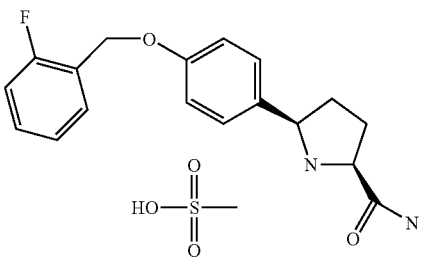

EtOAc (6 ml) was added to (5R)-5-(4-{[(2-Fluorophenyl)methyl]oxy}phenyl)-L-prolinamide (300 mg) and this was heated at 60° C. for an hour to dissolve the compound. Then methanesulfonic acid (65 μl, 1.05 eq) was added to the solution and as soon as the acid was added, the solution went cloudy. This was then left to temperature cycle (0-40° C.) for 2 days. The compound was isolated by filtration as a white solid, washed with EtOAc and dried in vacuo at 40° C. overweek-end to afford 335 mg of the title compound.

Melting point: 192° C.

Intermediate 20

1-(1,1-Dimethylethyl)2-methyl(2S,5R)-5-{4-[(phenyl methyl)oxy]phenyl}-1,2-pyrrolidinedicarboxylate

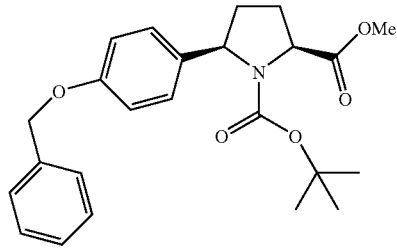

To a solution of methyl(5R)-5-{4-[(phenylmethyl)oxy]phenyl}-L-prolinate (2.6 g, 8.35 mmol) in DCM (30 ml) was added di-tert-butyl dicarbonate (2.0 g, 9.18 mmol). After stirring for 1 h at room temperature, the mixture was evaporated and the residue was purified by chromatography on silica gel using cyclohexane/ethyl acetate (9:1 to 85:15) to afford the title compound (3.29 g, 96%) as a white foam; R$_f$ (HPLC): 6.55 min; MS: (ES/+) m/z: 434 [M+Na⁺], 312 [M-BOC]; C₂₄H₂₉NO₅ requires 411; ¹H NMR (400 MHz, CDCl₃) δ (ppm): 7.52-7.43 (m, 4H); 7.43-7.37 (m, 2H); 7.37-7.30 (m, 1H); 6.96 (d, 2H); 5.09 and 5.06 (s, s, 2H); 4.99-4.93 and 4.52-4.44 (m, m, 1H); 4.76-4.68 and 4.39-4.32 (m, m, 1H); 3.82 (s, 3H); 2.36-2.26 (m, 1H); 2.26-2.15 (m, 1H); 2.12-2.01 (m, 1H); 2.01-1.88 (m, 1H); 1.42 and 1.17 (s, s, 9H).

Reference Description 21

1,1-Dimethylethyl(2S,5R)-2-(aminocarbonyl)-2-methyl-5-{4-[(phenylmethyl)oxy]phenyl}-1-pyrrolidinecarboxylate

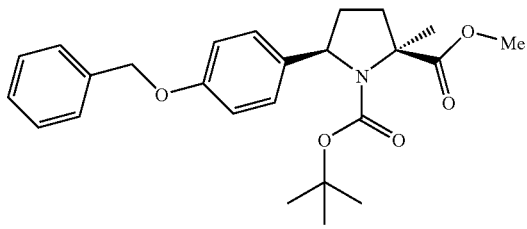

To a solution of 1-(1,1-dimethylethyl)2-methyl(2S,5R)-5-{4-[(phenylmethyl)oxy]phenyl}-1,2-pyrrolidinedicarboxylate (1.52 g, 3.7 mmol) in dry THF (27 ml) at −78° C. was added LiHMDS (4.0 ml, 4.0 mmol, 1M solution in THF). The mixture was allowed to warm to −20° C. and was stirred for 40 min at that temperature. Then the mixture was again cooled to −78° C. and methyl iodide (3.15 g, 22.1 mmol) was added. The mixture was left stirring for another 30 min at the same temperature. After standard work up, the organic layer was evaporated. The crude material was purified by chromatography on silica gel using cyclohexanes and ethyl acetate (1:0 to 9:1) affording the title compound (1.23 g, 78%); $R_t$ (HPLC): 6.76 min; MS: (ES/+) m/z: 448 [M+Na+]; C25H31NO5 requires 425; $^1$H NMR (400 MHz, CDCl$_3$) δ(ppm): 7.45-7.38 (m, 4H); 7.35 (t, 2H); 7.29 (t, 1H); 6.90 (d, 2H); 5.04 and 5.01 (s, s, 2H); 4.98 and 4.79 (d, d, 1H); 3.79 (s, 3H); 2.50-2.35 (m, 1H); 2.34-2.22 (m, 1H); 1.87-1.73 (m, 2H); 1.58 and 1.55 (s, s, 3H); 1.37 and 1.09 (s, s, 9H). NOE between the methyl group and the proton at C5 could be observed.

Intermediate 22

1-(1,1-Dimethylethyl)2-methyl(2R,5R)-2-(cyanomethyl)-5-{4-[(phenyl methyl)oxy]phenyl}-1,2-pyrrolidinedicarboxylate

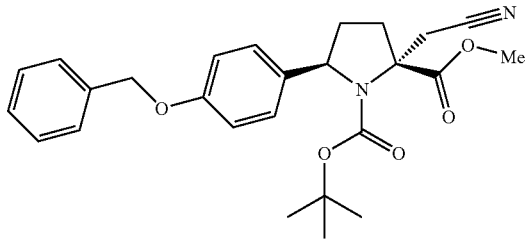

The title compound was prepared (2.71 g, 76%) using a similar procedure to as set out earlier in Reference Description 21 using crude 1-(1,1-dimethylethyl)2-methyl(2S,5R)-5-{4-[(phenylmethyl)oxy]phenyl}-1,2-pyrrolidinedicarboxylate (3.25 g, 7.89 mmol) and bromoacetonitrile (3.3 ml, 47.38 mmol in 40 ml THF); Rt (HPLC): 6.4 min; $R_f$(cyclohexane:ethyl acetate=7:3): 0.40; MS: (ES/+) m/z: 473 [M+Na+]; C26H30N2O5 requires 450; $^1$H NMR (500 MHz, DMSO-d$_6$) δ(ppm): 7.46-7.24 (m, 7H); 6.94 (d, 2H); 5.11 (s, 2H); 4.94-4.78 (m, 1H); 3.78 (s, 3H); 3.33 (d, 1H); 3.22 (d, 1H); 2.66-2.52 (m, 1H); 2.42-2.29 (m, 1H); 2.29-2.16 (m, 1H); 1.92-1.77 (m, 1H); 1.38-0.97 (br. s, 9H); NOE between the aromatic protons and the methyl ester could be observed.

Intermediate 23

1,1-Dimethylethyl(2R,5R)-2-(4-hydroxyphenyl)-6-oxo-1,7-diazaspiro[4.4]nonane-1-carboxylate

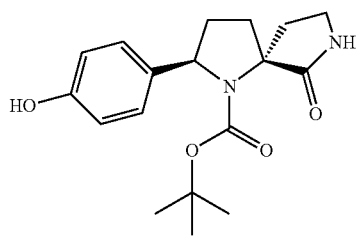

To a solution of 1-(1,1-dimethylethyl)2-methyl(2R,5R)-2-(cyanomethyl)-5-{4-[(phenylmethyl)oxy]phenyl}-1,2-pyrrolidinedicarboxylate (2.7 g, 5.99 mmol): in methanol (50 ml) was added Raney Nickel (slurry in water) and the mixture was stirred under a hydrogen atmosphere (7 atmospheres) for 14 hours. The catalyst was filtered off, the solvent removed under reduced pressure, and the solid residue was treated with toluene (3×20 ml) and dried under vacuum. The dry white solid obtained was refluxed in methanol (40 ml) for five hours until cyclization was complete. The solvent was removed under reduced pressure and the crude material purified by chromatography on silica gel using dichloromethane/methanol (95:5 to 90:10) to afford the title compound as a white solid (1.35 g, 68%); $R_f$ (HPLC): 3.91 min; $R_f$ (dichloromethane:methanol=9:1): 0.41; MS: (ES/+) m/z: 665 [2M+Na+], 355 [M+Na+]; C18H24N2O4 requires 332; $^1$H NMR (400 MHz, DMSO-d6) δ(ppm): 9.11 (s, 1H); 7.76 and 7.66 (s, s, 1H); 7.43 (dd, 2H); 6.66 (dd, 2H); 4.81-4.70 (m, 1H); 3.29-3.20 (m, 1H); 3.19-3.09 (m, 1H); 2.47-2.20 (m, 2H); 2.08-1.85 (m, 2H); 1.84-1.74 (m, 1H); 1.68-1.52 (m, 1H); 1.33 and 1.08 (s, s, 9H).

Reference Description 24

1,1-Dimethylethyl(2S,5R)-2-(aminocarbonyl)-5-(4-{[(2-fluorophenyl)methyl]oxy}phenyl)-2-methyl-1-pyrrolidinecarboxylate

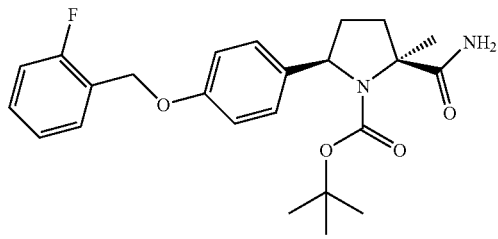

To a solution of 1,1-dimethylethyl(2S,5R)-2-(aminocarbonyl)-5-(4-hydroxyphenyl)-2-methyl-1-pyrrolidinecarboxylate (300 mg, 0.936 mmol) and potassium carbonate (194 mg, 1.4 mmol) in acetonitrile (4 ml) was added 1-(bromomethyl)-2-fluorobenzene (Sigma Aldrich Ltd.) (170 μl, 1.4 mmol) and the mixture was stirred overnight at room temperature. After the reaction was finished, as shown by TLC, ethyl acetate and water were added. The organic phase was then washed with brine, dried, filtered and evaporated. The crude material was purified by chromatography on silica gel using cyclohexane/ethyl acetate (8:2 to 7:3) to afford the title compound (306 mg, 72%); $R_t$(HPLC): 5.88 min; $R_f$(cyclohexane:ethyl acetate=1:1): 0.51; $^1$H NMR (300 MHz, DMSO-d6) δ(ppm): 7.60-7.49 (t, 2H); 7.46-7.32 (m, 2H); 7.29-7.15 (m, 3H); 7.13-7.02 (m, 1H); 6.98-6.88 (m, 2H); 5.11 (s, 2H); 4.87-4.62 (m, 1H); 2.41-2.16 (m, 2H); 1.78-1.64 (m, 1H); 1.64-1.56 (m, 1H); 1.52 (s, 3H); 1.32 and 1.03 (s, s, 9H).

Intermediate 25

1,1-Dimethylethyl(2R,5R)-2-(4-{[(2-fluorophenyl)methyl]oxy}phenyl)-6-oxo-1,7-diazaspiro[4.4]nonane-1-carboxylate

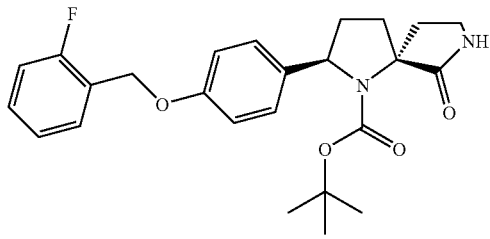

Method a):

The title compound was prepared using a similar procedure as set out earlier in Reference Description 42 starting from 1,1-dimethylethyl(2R,5R)-2-(4-hydroxyphenyl)-6-oxo-1,7-diazaspiro[4.4]nonane-1-carboxylate (850 mg, 2.55 mmol) and 2-fluorobenzyl bromide (0.5 ml, 3.83 mmol); $R_f$(HPLC): 5.72 min; $R_f$ (cyclohexane:ethyl acetate=3:7): 0.45; MS: (ES/+) m/z: 463 [M+Na$^+$]. C25H29FN2O4 requires 440; $^1$H NMR (400 MHz, CDCl$_3$) δ(ppm): 7.61 (d, 2H); 7.56-7.49 (m, 1H); 7.35-7.28 (m, 1H); 7.20-7.13 (m, 1H); 7.12-7.05 (m, 1H); 7.00-6.94 (dd, 2H); 5.64 and 5.61 (s, s, 1H); 5.14 and 5.12 (s, s, 2H); 5.08 and 4.88 (d, d, 1H); 3.58-3.40 (m, 1H); 3.38-3.24 (m, 1H); 2.82-2.56 (m, 1H); 2.43-2.21 (m, 2H); 2.15-2.00 (m, 1H); 1.95-1.75 (m, 2H), 1.45 and 1.17 (s, s, 9H).

Method b):

To a solution of 1-(1,1-dimethylethyl)2-methyl(2R,5R)-2-(cyanomethyl)-5-(4-{[(2-fluorophenyl)methyl]oxy}phenyl)-1,2-pyrrolidinedicarboxylate (51.3 g) in MeOH (~500 mL) was added CoCl$_2$.6H$_2$O (13.04 g). To the resulting purple solution were added three batches of NaBH$_4$ (8.29 g, 8.29 g and 4.145 g respectively; exothermic addition) portionwise every 30 minutes. The reaction mixture was cooled down to ambient temperature, filtered and the resulting solution was heated to reflux overnight. Then the mixture was cooled down and filtered. NH$_4$Cl saturated solution (513 mL) was added and MeOH evaporated in vacuo. The aqueous phase was extracted with EtOAc (2×500 mL) and the combined organic phase was evaporated to dryness and the crude material was purified by chromatography on silica gel pad using cyclohexane and ethyl acetate (1:1, 4:6, 3:7) affording the title compound (22.1 g) as a white solid.

1H NMR (400 MHz, CHCl$_3$-d) δ(ppm): 7.61 (m, 2H), 7.53 (m, 1H), 7.31 (m, 1H), 7.16 (m, 1H), 7.09 (m, 1H), 6.97 (m, 2H), 5.58 (s, 1H), 5.14 (m, 2H), 5.04-4.86 (m, 1H), 3.58-3.42 (m, 1H), 3.32 (m, 1H), 2.80-2.58 (m, 1H), 2.32 (m, 2H), 2.07 (m, 1H), 1.93-1.78 (m, 2H), 1.45 (s, 3H), 1.17 (s, 6H).

Intermediate 26

1,1-Dimethylethyl(2R,5R)-2-(4-{[(2-fluorophenyl)methyl]oxy}phenyl)-7-methyl-6-oxo-1,7-diazaspiro[4.4]nonane-1-carboxylate

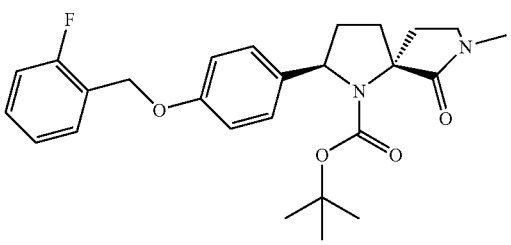

To a solution of 1,1-dimethylethyl(2R,5R)-2-(4-{[(2-fluorophenyl)methyl]oxy}phenyl)-6-oxo-1,7-diazaspiro[4.4]nonane-1-carboxylate (70 mg, 0.159 mmol) in dry DMF (1 ml) at 0° C. was added NaH 60% wt dispersion in mineral oil (10 mg, 0.238 mmol); after 15 minutes of stirring at room temperature, iodomethane (30 μl, 0.477 mmol) was added and the resulting mixture was stirred at room temperature for 2.5 hours. The mixture was cooled to 0° C., and water (4 ml) and ethyl acetate (10 ml) were added, the organic layer was washed with ice cold brine (3×10 ml), dried over Na$_2$SO$_4$ and evaporated. The crude material was purified by chromatography on silica gel using cyclohexanes/ethyl acetate (7:3) to afford the title compound as a white solid (63 mg, 88%); $R_t$ (HPLC): 5.99 min; $R_f$(cyclohexane:ethyl acetate=1:1): 0.28; MS: (ES/+) m/z: 477 [M+Na$^+$]; C26H31FN2O4 requires 454. $^1$H NMR (400 MHz, CDCl$_3$) δ(ppm): 7.66 (d, 2H); 7.56-7.49 (m, 1H); 7.35-7.25 (m, 1H); 7.20-7.13 (m, 1H); 7.12-7.04 (m, 1H); 6.97 (dd, 2H); 5.14 and 5.12 (s, s, 2H); 5.02 and 4.88 (d, d, 1H); 3.52-3.45 and 3.41-3.22 (m, m, 2H); 2.96 and 2.92 (s, s, 3H); 2.67-2.56 and 2.53-2.42 (m, m, 1H); 2.40-2.22 (m, 2H); 2.08-1.79 (m, 2H); 1.77-1.68 (m, 1H), 1.40 and 1.16 (s, s, 9H).

Intermediate 28

1-(1,1-Dimethylethyl)2-methyl(2S,5R)-5-(4-{[(2-fluorophenyl)methyl]oxy}phenyl)-1,2-pyrrolidinedicarboxylate

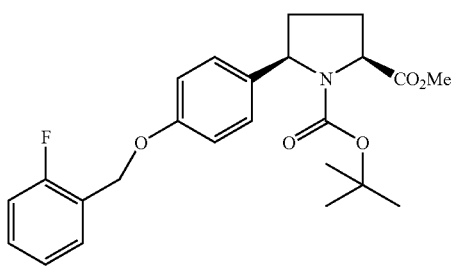

Methyl(5R)-5-(4-{[(2-fluorophenyl)methyl]oxy}phenyl)-L-prolinate (175 g) was dissolved in EtOAc (1000 mL) and cooled to 0° C. A solution of di-tert-butyl-dicarbonate (127.5 g) in EtOAc (750 mL) was added dropwise in about 1 hour maintaining the temperature at about 0° C. Then the temperature was increased to 25° C. and the reaction stirred at 25° C. for 2 hours. 28% w/w Racemic malic acid (350 mL) was added and the mixture stirred for about 10 min. The organic phase was washed with saturated NaHCO$_3$ (700 mL). Aqueous pH was ~8. The organic phase was concentrated to a low volume then stripped with cyclohexane (3×350 mL) to afford the title compound (240.8 g). $^1$H NMR (400 MHz, CDCl$_3$) δ(ppm): 7.54 (m, 1H); 7.50 (d, 2H); 7.33 (m, 1H); 7.18 (dt, 1H); 7.11 (m, 1H); 6.98 (d, 2H); 5.16 (2s, 2H); 4.97-4.46 (2 bm, 1H); 4.73-4.37 (2t, 1H); 3.83 (s, 3H); 2.32 (m, 1H); 2.21 (m, 1H); 2.08 (m, 1H); 1.96 (m, 1H); 1.43-1.18 (2 bs, 9H).

Intermediate 29

1-(1,1-Dimethylethyl)2-methyl(2R,5R)-5-(4-{[(2-fluorophenyl)methyl]oxy}phenyl)-2-(2-propen-1-yl)-1,2-pyrrolidinedicarboxylate

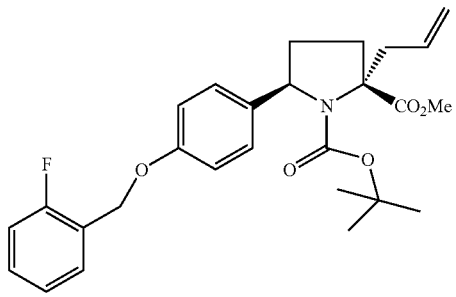

The previous crude of 1-(1,1-dimethylethyl)2-methyl(2S,5R)-5-(4-{[(2-fluorophenyl)methyl]oxy}phenyl)-1,2-pyrrolidinedicarboxylate was split in two batches. The first one (100 g) was dissolved in dry THF (1000 mL) then allyl bromide (42.25 g) was added, finally the mixture was cooled to −30° C. 1M LiHMDS in THF (439 mL) was added dropwise in about 1.5 hours maintaining the temperature at about −30° C. Water (100 mL) was added and temperature allowed to reach 0° C. Saturated NH$_4$Cl (500 mL) was added followed by water (400 mL) and EtOAc (500 mL). The reaction was warmed to 25° C. and the aqueous layer was removed. The organic layer was concentrated to about 700 mL and washed with NaHCO$_3$ saturated solution (200 mL). Organic layer was dried over Na$_2$SO$_4$ and concentrated to afford the title compound as an oil (119.8 g). The second batch (135 g) was similarly reacted using dry THF (1350 mL), allyl bromide (57.04 g) and 1M LiHMDS in THF (471.5 mL). After work-up, the title compound was isolated as an oil (179 g). $^1$H NMR (400 MHz, DMSO-d$_6$) δ(ppm): 7.53 (m, 1H); 7.39 (m, 3H); 7.22 (m, 2H); 6.95 (m, 2H); 5.82 (m, 1H); 5.12 (m, 4H); 4.80-4.59 (2m, 1H); 3.74-3.71 (2s, 3H); 3.01-1.52 (m, 6H); 1.29-0.98 (2s, 9H).

Intermediate 30

1-(1,1-Dimethylethyl)2-methyl(2R,5R)-2-(2,3-dihydroxypropyl)-5-(4-{[(2-fluorophenyl)methyl]oxy}phenyl)-1,2-pyrrolidinedicarboxylate The reaction was performed on the two separated batches of 1-(1,1-dimethylethyl)2-methyl(2R,5R)-5-(4-{[(2-fluorophenyl)methyl]oxy}phenyl)-2-(2-propen-1-yl)-1,2-pyrrolidinedicarboxylate obtained from the previous step. The first batch (119.8 g) was dissolved in a mixture of 10/1 acetone/water (1200 mL). K$_2$OsO$_4$.2H$_2$O (4.7 g) was added followed by NMO (41.4 g) after a few minutes. The mixture was stirred for 7.5 hours. The reaction mixture was treated with EtOAc (1200 mL) and washed with saturated NH$_4$Cl (1200 mL) then with saturated NaHCO$_3$ (1200 mL). The organic layer was filtered through a celite/activated charcoal pad and concentrated to low volume. EtOAc (500 mL) was added and the solution was washed with brine (300 mL) and the organic dried over Na$_2$SO$_4$, and evaporated to dryness, EtOAc (300 mL) was added and filtered through CUNO filter and washed with EtOAc (50 mL). The organic was concentrated to dryness to afford the title compound (135 g). The second batch (179 g) was dissolved in a mixture of 10/1 acetone/water (1800 mL). K$_2$OsO$_4$.2H$_2$O (5.5 g) was added followed by NMO (56.8 g) after a few minutes. The mixture was stirred overnight at room temperature. The reaction mixture was treated with EtOAc (900 mL) and washed with saturated NH$_4$Cl (2×900 mL) then with saturated NaHCO$_3$ (900 mL). The organic layer was filtered through a celite pad and concentrated to low volume to afford the title compound (250 g). $^1$H NMR (400 MHz, DMSO-d$_6$) δ(ppm): 7.54 (m, 1H); 7.40

(m, 3H); 7.22 (m, 2H); 6.95 (m, 2H); 5.11 (m, 2H); 4.95-4.25 (m, 3H); 3.70 (bm, 3H); 3.50-3.10 (m, 3H); 2.50-1.50 (m, 6H); 1.30-0.95 (4 bs, 9H).

Intermediate 31

1-(1,1-Dimethylethyl)2-methyl(2R,5R)-5-(4-{[(2-fluorophenyl)methyl]oxy}phenyl)-2-(2-oxoethyl)-1,2-pyrrolidinedicarboxylate

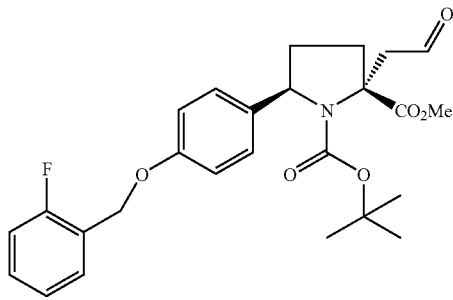

Procedure 1: The reaction was performed on the two separated batches of 1-(1,1-dimethylethyl)2-methyl(2R,5R)-2-(2,3-dihydroxypropyl)-5-(4-{[(2-fluorophenyl)methyl]oxy}phenyl)-1,2-pyrrolidinedicarboxylate obtained from the previous step. The first batch (135 g) was dissolved in a mixture of 10/1 acetone/water (2000 mL) and $NaIO_4$ (74.54 g) was added. The solution turned from brown to yellow and a suspension was formed. The mixture was stirred overnight at 25° C. Further $NaIO_4$ (2×5.73 g) was added and stirred for further 24 hours. EtOAc (1000 mL) was added followed by water (1000 mL). After mixing the aqueous phase was removed. The organic phase was concentrated to a yellow oil and stripped with EtOAc (250 mL) to afford the title compound (109 g). The second batch (250 g) was dissolved in a mixture of 10/1 acetone/water (1900 mL) and $NaIO_4$ (106 g) was added. The solution turned from brown to yellow and a suspension was formed. The mixture was stirred for 6 hours then further $NaIO_4$ (8.15 g) was added and stirred overnight. EtOAc (1000 mL) was added followed by water (2000 mL). After mixing the aqueous phase was removed. The organic phase was concentrated to a yellow oil and stripped with EtOAc (300 mL) to afford the title compound (180 g).

$^1H$ NMR (400 MHz, DMSO-$d_6$) δ(ppm): 9.72 (m, 1H); 7.56 (m, 1H); 7.42 (m, 3H); 7.24 (m, 2H); 6.99 (m, 2H); 5.14 (m, 2H) 4.90-4.79 (2m, 1H); 3.80-3.77 (2s, 3H); 3.02 (m, 1H); 2.83 (m, 1H); 2.55-1.55 (m, 4H); 1.32-1.03 (2s, 9H).

Procedure 2: A solution of 1-(1,1-dimethylethyl)2-methyl(2R,5R)-5-(4-{[(2-fluorophenyl)methyl]oxy}phenyl)-2-(2-propen-1-yl)-1,2-pyrrolidinedicarboxylate (15 g) in methanol (200 ml) was cooled to −10° C. Ozone gas was passed through the solution for 2 hours, then the mixture was warmed to 0-5° C. Dimethylsulphide (7.04 ml) was added and the mixture stirred for 1 hours at 0-5° C., then at room temperature for 3 hours. The mixture was then concentrated under vacuum at 35-50° C. to give a residue. This was treated with water (45 ml), then extracted with DCM (2×37.5 ml). The combined extracts were stirred with a mixture of 60-120 mesh silica gel (45 g, DCM (75 ml) and 10% oxalic acid (6 ml) for 4 hours. The mixture was then filtered and washed with DCM (75 ml). The combined filtrates were washed with water (75 ml) and 10% sodium bicarbonate (75 ml) and water (75 ml). The solution was then dried over sodium sulphate and evaporated, then dried under vacuum to give the title compound as a brownish yellow pasty mass (12.7 g).

Intermediate 32

1-(1,1-Dimethylethyl)2-methyl(2R,5R)-5-(4-{[(2-fluorophenyl)methyl]oxy}phenyl)-2-[2-(methylamino)ethyl]-1,2-pyrrolidinedicarboxylate

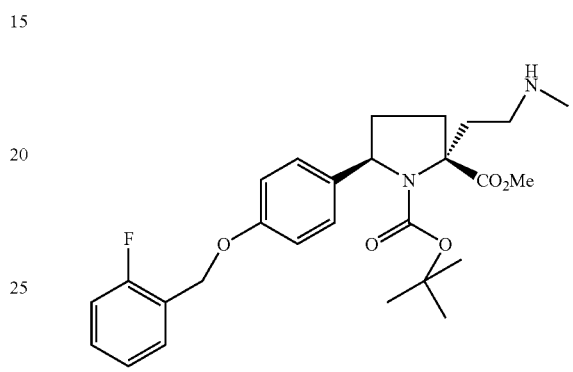

The reaction was performed on the two separated batches of 1-(1,1-dimethylethyl)2-methyl(2R,5R)-5-(4-{[(2-fluorophenyl)methyl]oxy}phenyl)-2-(2-oxoethyl)-1,2-pyrrolidinedicarboxylate obtained from the previous step (148, Procedure 1). The first batch (109 g) was dissolved in MeOH (440 mL) and $MeNH_2$ in MeOH 2M solution (347 mL) was added. AcOH (11 mL) was added. $NaBH(OAc)_3$ (49 g) was added portion wise after 10 minutes. More $NaBH(OAc)_3$ (14.7 g) was added portion wise at 25° C. The reaction mixture was quenched with 28% aqueous malic acid (200 mL) followed by AcOEt (1000 mL). $K_2CO_3$ was added up to pH~9. Organic phase was concentrated to dryness, re-dissolved in EtOAc (500 mL) and extracted with 20% citric acid (4×300 mL). The combined aqueous phases were treated with EtOAc (500 mL) and solid $K_2CO_3$ was added until pH~9. The phases were separated and the organic phase was dried under $Na_2SO_4$ and evaporated to dryness to afford the title compound (80 g). The second batch (180 g) was dissolved in MeOH (628 mL) and $MeNH_2$ in MeOH 2M solution (300 mL) was added. AcOH (31 mL) was added. $NaBH(OAc)_3$ (78.8 g) was added portionwise at 0° C. after 10 minutes. The reaction mixture was quenched with saturated $NH_4Cl$ (890 mL) and EtOAc (890 mL). The phases were separated and the aqueous was extracted with EtOAc (4×300 mL). The organic phase was dried over $Na_2SO_4$, concentrated to dryness, re-dissolved in EtOAc (500 mL) and extracted with 20% citric acid (6×150 mL). The combined aqueous phases were treated with EtOAc (600 mL) and solid $K_2CO_3$ was added until pH 8/9. The Phases were separated and the organic phase dried over $Na_2SO_4$ and evaporated to dryness to afford the title compound (78 g). $^1H$ NMR (400 MHz, DMSO-$d_6$) δ(ppm): 7.55 (m, 1H); 7.42 (m, 3H); 7.25 (m, 2H); 6.98 (m, 2H); 5.14

(m, 2H); 4.85-4.69 (2m, 1H); 3.75-3.73 (2s, 3H); 2.36 (bs, 3H) 2.80-2.25 (m, 2H); 2.20-2.00 (m, 3H); 1.70 (m, 1H); 1.32-1.00 (2s, 9H).

Intermediate 33

1-(1,1-Dimethylethyl)2-methyl(2R,5R)-2-(cyanomethyl)-5-(4-{[(2-fluorophenyl)methyl]oxy}phenyl)-1,2-pyrrolidinedicarboxylate

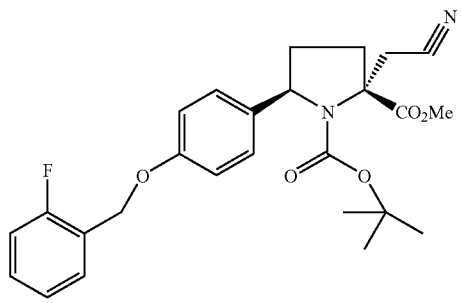

To a solution of 1-(1,1-dimethylethyl)2-methyl(2S,5R)-5-(4-{[(2-fluorophenyl)methyl]oxy}phenyl)-1,2-pyrrolidinedicarboxylate (45 g) in dry THF (450 mL) previously cooled to −65° C., was added 1M LiHMDS in THF (115 mL) dropwise. The resulting solution was stirred at −35° C. for 30 minutes. Then the mixture was again cooled to −65° C. and bromoacetonitrile (22 mL) dissolved in dry THF (180 mL) was added. The mixture was left stirring for a further 30 min at the same temperature. The reaction was quenched with saturated ammonium chloride solution (675 mL), THF was evaporated in vacuo and the crude mixture was extracted with EtOAc (2×675 mL). The organic layer was evaporated and the crude material was purified by chromatography on silica gel using cyclohexanes and ethyl acetate (8:2) affording the title compound (51.3 g) as a yellow thick oil.

1H NMR (400 MHz, CDCl$_3$-d) δ(ppm): 7.53 (t, 1H), 7.43 (d, 2H), 7.29-7.37 (m, 1H), 7.17 (t, 1H), 7.07-7.13 (m, 1H), 6.97 (d, 2H), 5.16 (s, 2H), 4.88-4.95 (m, 1H), 3.90 (s, 3H), 3.52 (d, 1H), 3.15 (d, 1H), 2.57-2.70 (m, 1H), 2.38-2.50 (m, 1H), 2.23-2.34 (m, 1H), 1.92-2.06 (m, 1H), 1.44 (s, 9H).

Intermediate 34

1-(1,1-dimethylethyl)2-methyl(2R,5R)-5-(4-{[(2-fluorophenyl)methyl]oxy}phenyl)-2-[2-(methylamino)ethyl]-1,2-pyrrolidinedicarboxylate and 1,1-dimethylethyl(2R,5R)-2-(4-{[(2-fluorophenyl)methyl]oxy}phenyl)-7-methyl-6-oxo-1,7-diazaspiro[4.4]nonane-1-carboxylate

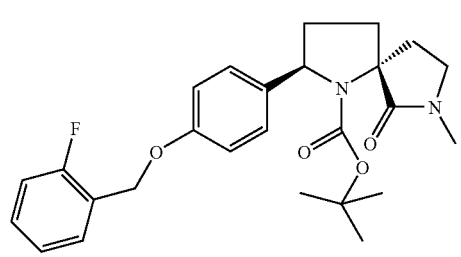

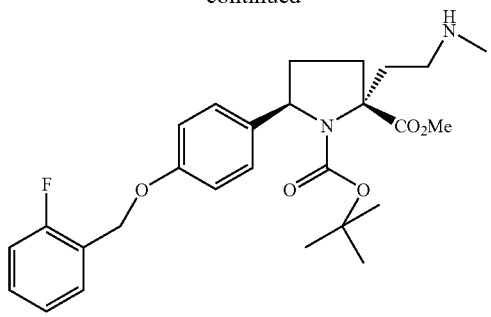

A solution of 1-(1,1-dimethylethyl)2-methyl(2R,5R)-5-(4-{[(2-fluorophenyl)methyl]oxy}phenyl)-2-(2-oxoethyl)-1,2-pyrrolidinedicarboxylate (148, 9.5 g) in methanol (38 ml) was cooled to 5-10° C. Methylamine in methanol (12.7 g of a 24.7% solution) was added and the mixture stirred at 5-10° C. for 1 hour. Acetic acid (7.6 ml) was added to give a pH of approximately 7, and then the temperature was raised to 20-25° C. Sodium triacetoxyborohydride (6.4 g) was added in portions over 1 hour, then the mixture stirred at 20-25° C. for a further 2 hours. Methanol was distilled off under vacuum, then the mixture treated with ethyl acetate (50 ml) and water (50 ml). The layers were separated and the aqueous layer re-extracted with ethyl acetate (25 ml). The combined ethyl acetate solutions were extracted with 28% citric acid solution (4×50 ml), then the combined aqueous layers were treated with 30% sodium carbonate solution (150 ml) and ethyl acetate to pH 9. The aqueous layer was re-extracted with ethyl acetate (25 ml), then the combined ethyl acetate solution was dried over sodium sulphate and evaporated to give the title compound as a crude (6.6 g) also comprising the compound 1,1-dimethylethyl (2R,5R)-2-(4-{[(2-fluorophenyl)methyl]oxy}phenyl)-7-methyl-6-oxo-1,7-diazaspiro[4.4]nonane-1-carboxylate.

MS: (ES/+) m/z: 455 [MH$^+$] (cyclised product)

Representative Na Channel Blocker Example 11 (ENa11)

(2R,5R)-2-(4-{[(2-Fluorophenyl)methyl]oxy}phenyl)-7-methyl-1,7-diazaspiro[4.4]nonan-6-one

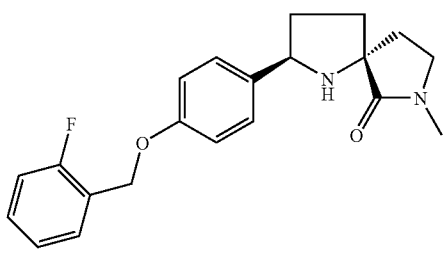

Procedure 1: The reaction was performed on the two separated batches of 1-(1,1-dimethylethyl)2-methyl(2R,5R)-5-(4-{[(2-fluorophenyl)methyl]oxy}phenyl)-2-[2-(methylamino)ethyl]-1,2-pyrrolidinedicarboxylate resulting from procedure described for Intermediate 49.

The first batch (80 g) was dissolved in MeOH (320 mL), 5-6N HCl in IPA (160 mL) was added and the mixture stirred overnight at 25° C. 13% aqueous NH$_3$ (200 mL) was added, cooling the reaction to 0° C. during addition, until complete conversion. EtOAc (320 mL), water (160 mL) and NaHCO$_3$ saturated solution (240 mL) were added and the phases separated. Aqueous phase was extracted with EtOAc (6×80 mL) and the organic phase was concentrated to about 400 mL then washed with brine (120 mL) which was back extracted with EtOAc (80 mL). The combined organic phases were dried over Na$_2$SO$_4$ and evaporated to dryness to afford the crude (50 g).

The second batch (81 g) was dissolved in MeOH (324 mL), 5-6N HCl in IPA (162 mL) was added and the mixture stirred overnight at 25° C. Further 5-6N HCl in IPA (20 mL) was added and stirred for a further 6 hours. NaHCO$_3$ saturated solution (160 mL) and EtOAc (500 mL) were added followed by solid NaHCO$_3$ to pH-8. Phases were separated and the aqueous was back extracted with EtOAc (2×200 mL). Combined organics were concentrated to about 400 mL. DCM (300 mL) and brine (200 mL) were added, the phases were separated and the organic phase was dried over Na$_2$SO$_4$ and evaporated to dryness to afford crude (67 g). DCM (135 mL) was added and stirred overnight at room temperature then heated to reflux for 3 hours then cooled back to room temperature. 2M NH$_3$ in methanol (12.5 mL) was added due to incomplete cyclisation and then aqueous 13% NH$_3$ was added and stirred for at least 2 hours to reach complete cyclisation. Brine (100 mL) was added, phases were separated and organic was dried over Na$_2$SO$_4$ and evaporated to dryness to afford the crude (58 g).

The two crudes were combined and purified via chromatographic column (DCM/MeOH 25/1) to afford the title compound (85 g).

$^1$H NMR (600 MHz, DMSO-d$_6$) δ(ppm): 7.56 (dt, 1H); 7.41 (m, 3H); 7.25 (t, 1H); 7.23 (t, 1H); 6.97 (d, 2H); 5.12 (s, 2H); 4.18 (m, 1H); 3.28 (m, 1H); 3.21 (m, 1H); 2.77 (s, 3H); 2.50 (bs, 1H); 2.12 (m, 1H); 2.01 (m, 1H); 1.92 (m, 1H); 1.72 (m, 2H).

Procedure 2: A mixture of 1-(1,1-dimethylethyl)2-methyl (2R,5R)-5-(4-{[(2-fluorophenyl)methyl]oxy}phenyl)-2-[2-(methylamino)ethyl]-1,2-pyrrolidinedicarboxylate and 1,1-dimethylethyl(2R,5R)-2-(4-{[(2-fluorophenyl)methyl]oxy}phenyl)-7-methyl-6-oxo-1,7-diazaspiro[4.4]nonane-1-carboxylate (5.8 g) was dissolved in MeOH (23.2 mL), HCl in IPA (14.3% solution, 17.7 g) was added and the mixture stirred at 25° C. for 24 hours. 13% aqueous NH$_3$ (14.5 ml) and the mixture stirred for 4 hours. EtOAc (60 mL) and water (40 mL) were added and the phases separated. The aqueous phase was extracted with EtOAc (25 ml) then the combined organic phases were dried over Na$_2$SO$_4$ and evaporated to dryness to afford the crude (5.52 g). The crude was purified via column chromatography (EtOAc to 9:1 EtOAc/MeOH) to afford the title compound (2.1 g).

Representative Na Channel blocker Example 12
(ENa12)

(2R,5R)-2-(4-{[(2-fluorophenyl)methyl]oxy}phenyl)-7-methyl-1,7-diazaspiro[4.4]nonan-6-one 4-methylbenzenesulfonate

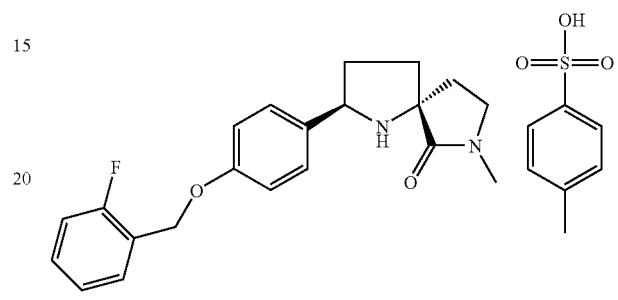

The compound (2R,5R)-2-(4-{[(2-fluorophenyl)methyl]oxy}phenyl)-7-methyl-1,7-diazaspiro[4.4]nonan-6-one hydrochloride (57.2 g) was suspended in EtOAc (286 mL) and NaHCO$_3$ saturated solution (229 mL) was added. The layers were separated and the organic layer was dried over Na$_2$SO$_4$.

The salt was filtered off and washed with EtOAc (3×57 mL).

The solvent was evaporated under reduced pressure and the crude stripped with acetone (2×171 mL), giving 52.7 g of (2R,5R)-2-(4-{[(2-fluorophenyl)methyl]oxy}phenyl)-7-methyl-1,7-diazaspiro[4.4]nonan-6-one.

This compound was dissolved in acetone (520 mL) and the solution was heated to 40° C. A solution of p-toluenesulfonic acid monohydrate (27.84 g) in acetone (260 mL) was added in 30 min.

A solid precipitated after the addition of approx 50 mL of this solution.

The mixture was stirred at 40° C. for 4.5 h and then cooled to room temperature.

The solid was collected, washed with acetone (3×230 mL) and dried under high vacuum for 16 hours obtaining the Form 1 crystals of the title compound (70.1 g).

$^1$H NMR (400 MHz, DMSO-d6) δ(ppm): 9.90 (bs, 1H); 8.91 (bs, 1H); 7.55 (m, 3H); 7.48 (m, 2H); 7.43 (m, 1H); 7.25 (m, 2H); 7.11 (m, 4H); 5.18 (s, 2H); 4.73 (dd, 1H); 3.41 (m, 2H); 2.82 (s, 3H); 2.36 (m, 5H); 2.29 (s, 3H); 2.11 (m, 1H).

Unique and discriminating peaks of Form 1 of Example 12 have been identified and are illustrated in the table below:

| Position [°2Th.] | d-spacing [Å] |
| --- | --- |
| 6.8 | 13.0 |
| 8.7 | 10.2 |
| 10.8 | 8.2 |
| 12.7 | 7.0 |
| 13.6 | 6.5 |
| 14.6 | 6.1 |
| 17.3 | 5.1 |
| 17.8 | 5.0 |
| 18.3 | 4.8 |

| Position [°2Th.] | d-spacing [Å] |
|---|---|
| 20.4 | 4.4 |
| 21.0 | 4.2 |
| 22.0 | 4.0 |
| 22.6 | 3.9 |
| 23.1 | 3.8 |
| 24.1 | 3.7 |
| 24.6 | 3.6 |
| 25.0 | 3.6 |
| 27.2 | 3.3 |
| 27.8 | 3.2 |
| 28.1 | 3.2 |
| 28.7 | 3.1 |
| 29.3 | 3.0 |
| 29.6 | 3.0 |
| 30.2 | 3.0 |
| 34.6 | 2.6 |
| 35.4 | 2.5 |
| 36.1 | 2.5 |
| 44.5 | 2.0 |

Melting point: 233° C.

Representative Na Channel Blocker Example 13 (ENa13)

(2R,5R)-2-(4-{[(2-Fluorophenyl)methyl]oxy}phenyl)-7-methyl-1,7-diazaspiro[4,4]nonan-6-one hydrochloride

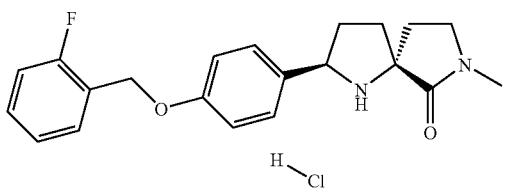

Procedure 1: To a solution of 1,1-dimethylethyl(2R,5R)-2-(4-{[(2-fluorophenyl)methyl]oxy}phenyl)-7-methyl-6-oxo-1,7-diazaspiro[4.4]nonane-1-carboxylate (61 mg, 0.134 mmol) in a mixture of ethyl acetate (1 ml) and methanol (0.1 ml) at 0° C. was added acetyl chloride (60 µl, 0.806 mmol). The mixture was stirred for 3 hours at room temperature. The solvent was removed under vacuum and the gummy solid was treated with Et$_2$O (3×2 ml) obtaining a white solid (53 mg). R$_t$ (HPLC): 3.72 min; MS: (ES/+) m/z: 355 [MH$^+$]; C21H23FN2O2 requires 354; $^1$H NMR (500 MHz, DMSO-d$_6$) δ (ppm): 10.58 (br. s., 1H), 8.87 (br. s., 1H), 7.59-7.52 (m, 3H), 7.47-7.39 (m, 1H), 7.31-7.20 (m, 2H), 7.11 (d, 2H), 5.17 (s, 2H), 4.80-4.66 (m, 1H), 3.43-3.37 (m, 2H), 2.81 (s, 3H), 2.59-2.23 (m, 5H), 2.13-2.03 (m, 1H).

Procedure 2: The previous crude of (2R,5R)-2-(4-{[(2-fluorophenyl)methyl]oxy}phenyl)-7-methyl-1,7-diazaspiro[4.4]nonan-6-one (75.85 g) was stripped with Et$_2$O (2×150 mL), dissolved in DCM (150 mL) and 5-6M HCl in IPA (76 mL) was added at room temperature. Solvent and excess of HCl were evaporated and then stripped with Et$_2$O (2×76 mL) and DCM (2×76 mL) to get a foam. The foam was suspended in Et$_2$O (600 mL) and DCM (76 mL) and stirred overnight at room temperature. Finally the solid was collected, washed with a mixture of Et$_2$O/DCM 8/1 (3×76 mL) and dried under high vacuum at 40° C. overnight to afford the title compound (79 g).
$^1$H NMR (500 MHz, DMSO-d$_6$) δ(ppm): 10.58 (bs, 1H); 8.87 (bs, 1H); 7.55 (m, 3H); 7.43 (m, 1H); 7.25 (m, 2H); 7.11 (d, 2H); 5.17 (s, 2H); 4.73 (m, 1H); 3.40 (m, 2H); 2.81 (s, 3H); 2.60-2.20 (m, 5H); 2.08 (m, 1H).

Intermediate 35

2-(2,3-Dichlorophenyl)-3-ethoxy-4-fluoro-2-butenenitrile

To a suspension of 2,3-dichlorophenylacetonitrile (45 kg, 241.9 mole) in methanol (90 litres) was charged 30% w/w sodium methoxide in methanol solution (113.5 kg, 630.6 mole) then ethylfluoroacetate (29.7 kg, 280.1 mole). The reaction mixture was stirred overnight and the product was precipitated from aqueous hydrochloric acid (63.7 kg, 648 mole) in water (350 litres). The slurry was filtered and the solid was dissolved in ethyl acetate and washed with brine solution. Ethyl acetate (100 litres) was removed by vacuum distillation. DMF (70 litres) was added and the distillation continued to remove the remaining ethyl acetate.

To the resulting enol in DMF was added potassium carbonate (20 kg, 145 mole) over a period of 10 minutes. Alkylation of the potassium enolate was achieved using ethyl iodide (37.7 kg, 241.9 mole) at 70° C. for 1¼ hours. The reaction mixture was partitioned between toluene (140 litres) and water (75 litres) and the toluene phase was washed with water (50 litres). Toluene (75 litres) was removed by distillation to afford the crude product as a toluene solution.

Intermediate 36

(+/−) 2,4-Diamino-5-(2,3-dichlorophenyl)-6-fluoro methylpyrimidine

To guanidine hydrochloride (25.4 kg, 266 mole) in methanol (60 litres) was added 30% w/w sodium methoxide in methanol solution (49.2 kg, 273.3 mole). The suspension was heated to 55° C.±2° C. The toluene solution of 2-(2,3-dichlorophenyl)-3-ethoxy-4-fluoro-2-butenenitrile was added over a period of 45 minutes and the resultant mixture was boiled under reflux for 4 hours, cooled then quenched into water (230 litres). The solid precipitate was washed with 5 portions of methanol (25 litres) to yield the racemate as an off white solid (26.3 kg, 38% yield from 2,3-dichlorophenylacetonitrile).

Representative Na Channel Blocker Example 14 (ENa14)

R(−)-2,4-diamino-5-(2,3-dichlorophenyl)-6-fluoromethyl pyrimidine

Procedure 1:
To racemic (+/−)2,4-diamino-5-(2,3-dichlorophenyl)-6-fluoromethylpyrimidine (0.8006 g) in a flask was added (−)-dibenzoyl-L-tartaric acid.H$_2$O (1.0490 g). Absolute ethanol (27.7 ml) was added, the mixture was warmed and the resulting solution was left overnight. The mother liquor was then decanted from the white crystalline solid that had formed. The solid was dried in a vacuum oven at 50° C. overnight. The yield of crystalline material obtained (0.9534 g) was about 52%.

The ratio of R(−)-2,4-diamino-5-(2,3-dichlorophenyl)-6-fluoromethyl pyrimidine ("R(−)enantiomer") to S(+)-2,4-diamino-5-(2,3-dichlorophenyl)-6-fluoromethyl pyrimidine ("S(+)enantiomer") was 81:19.

Crystalline material (0.8796 g) obtained in the initial resolution step 1 was dissolved under warming in absolute ethanol (36 ml). The solution was left to cool overnight. The mother liquor was decanted. The white crystalline solid obtained was dried in a vacuum oven at 50° C. overnight; yield (0.6111 g) 69%. The ratio of R(−)enantiomer to S(+)enantiomer was 94:6%.

Recrystallised material (0.5227 g) from step 2 was dissolved under warming in absolute ethanol (25 ml). The resulting solution was left to cool overnight. The mother liquor was then decanted. The remaining white crystalline solid was washed with ethanol (1 ml) and dried at 50° C. in a vacuum oven overnight; yield (0.397 g) 76%. The ratio of R(−) enantiomer to S(+)enantiomer was 99.8:0.2.

The crystalline salt from step 3 was then basified with 2M NaOH solution. Thus, distilled water was added to the salt. The resulting slurry was stirred at room temperature. Then 2M NaOH was added until pH 12 was maintained. The resulting suspension was left for 1 hour. Then the solid was filtered off and washed with water. The wet solid was dried at 50° C. in vacuo to give a white solid.

Procedure 2:

To racemic (+/−)2,4-diamino-5-(2,3-dichlorophenyl)-6-fluoromethyl pyrimidine (78.83 g) in a flask, (−)-dibenzoyl-L-tartaric acid.$H_2O$ (103.27 g) was added followed by absolute ethanol (2727 ml). The mixture was heated to reflux until all solids were in solution. The solution was left over 18 hours to cool to room temperature. The white solid formed was filtered off and dried in vacuo for 3 hours at 50° C. The dried solid was recrystallised from absolute ethanol twice (2×1500 ml). The white crystalline solid obtained was dried at 50° C. in vacuo for 6 hours. The ratio of R(−)enantiomer to S(+) enantiomer in the dried crystalline material obtained (22 g) was >99:1.

The mother liquors from the recrystallisations were concentrated in vacuo and then treated with 2M NaOH (aqueous solution) to basify the salt. Thus, water (100 ml) was added to the salt (98 g) followed by 2M NaOH solution (250 ml) in 50 ml portions while the suspension was vigorously stirred. The suspension was maintained at pH 12 for 2 hours. The white solid was filtered off and washed with water (5×50 ml) until pH7 was maintained. The solid was dried in vacuo at 50° C. for 4 hours to afford the free base (39 g). The ratio of R(−) enantiomer to S(+)enantiomer in the dried free base was 30:70.

The free base enriched with the S(+) enantiomer was then recycled to the racemate. Thus, toluene (500 ml) was added to the free base (39 g). The mixture was heated at reflux for 24 hours and then cooled to room temperature. A brown solid was filtered off which was dried in vacuo at 50° C. for 3 hours. The ratio R(−)enantiomer: S(+)enantiomer in the dried material obtained (33 g) was 50:50.

This racemate was then submitted to step 1 to obtain more of the R (−)enantiomer of >99% enantiomeric purity. The combined salts were then basified with 2M NaOH solution. Thus, distilled water (250 ml) was added to the salts (86.6 g) and the slurry stirred at room temperature. Then 2M NaOH (154 ml) was added in 50 ml portions and then two 2 ml portions until pH 12 was maintained. The resulting suspension was left for 1 hour and then the solid was filtered off and washed with water (7×100 ml). The wet solid was dried at 50° C. in vacuo to give, for this batch, a buff-coloured solid (37.9 g). Other batches however gave a white solid. The ratio of the R(−)enantiomer to the S(+)enantiomer in the dried material was 99.7:0.3.

Chemical purity=99.2%

PROPERTIES OF R(−)-2,4-DIAMINO-5-(2,3-DICHLOROPHENYL)-6-FLUOROMETHYL PYRIMIDINE

1. Chemical/Physico-Chemical Properties

| | |
|---|---|
| Physical appearance: | white solid |
| Melting point: | 215-216° C. |
| Molecular formula: | $C_{11}H_9Cl_2FN_4$ |
| Molecular weight: | 287.13 |
| Optical rotation: | $[\alpha]^{25.5}_D = -56.75°$ (c = 0.53, EtOH) |
| | $[\alpha]^{25.5}_{Hg546} = -72.07°$ (c = 0.53, EtOH) |
| Optical rotation for S(+)enantiomer: | $[\alpha]^{25.5}_D = +59.20°$ (c = 0.52, EtOH) |
| | $[\alpha]^{25.5}_{Hg546} = +70.00°$ (c = 0.52, EtOH) |
| NMR data: | 7.65 (dd, 1H, 4'); 7.39 (t, 1H, 5'); 7.23 (dd, 1H, 6'); 6.15 (s, 2H, 2-$NH_2$); 5.98 (s, 2H, 4-$NH_2$); 4.88 (quartet (q), 1H, $CH_2F$); 4.64 (q, 1H, $CH_2F$) |

Representative Na Channel Blocker Example 15 (ENa15)

R(−)-2,4-diamino-5-(2,3-dichlorophenyl)-6-fluoromethyl pyrimidine methanesulphonate Methanesulphonic acid (0.158 ml, 0.234 g, 2.39×10⁻³ mole) was added to a suspension of R(−)-2,4-diamino-5-(2,3-dichlorophenyl)-6-fluoromethyl pyrimidine in dry ether (21 ml). The resulting mixture was stirred at room temperature for 2 hrs. The suspension was filtered, washed well with dry ether (5 ml), sucked dry and dried under vacuum at room temperature.

| | |
|---|---|
| Yield | 0.911 g (93%) |
| M.p. | 245-247° C. |

Biological Assays

The ability of a compound to act as an NK1 receptor antagonist may be determined using the gerbil foot tapping model as described by Rupniak & Williams, Eur. Jour. of Pharmacol., 1994.

The compound is orally administered and four hours later an NK1 agonist (e.g. delta-Aminovaleryl⁶[Pro⁹,Me-Leu¹⁰]-substance P (7-11)) (3 µmol in 5 µL icv) is infused directly in the cerebral ventricules of the animals. The duration of hind foot tapping induced by the NK1 agonist (e.g. delta-Aminovaleryl⁶[Pro⁹,Me-Leu¹⁰]-substance P (7-11)) is recorded continuously for 3 min using a stopclock. The dose of the test compound required to inhibit by 50% the tapping induced by the NK1 agonist (e.g. delta-Aminovaleryl⁶[Pro⁹,Me-Leu¹⁰]-substance P (7-11)) expressed as mg/kg is referred to as the ED50 value. Alternatively the compounds may be administered subcutaneously or intraperitoneally.

The ability of the compounds of the invention to modulate the voltage-gated sodium channel subtype NaV 1.3 may be determined by the following assay.

Cell Biology

Stable cell lines expressing hNaV1.3 channels were created by transfecting CHO cells with the pCIN5-hNav1.3 vector using the lipofectamine (Invitrogen) transfection method.

pCIN5 is a bicistronic vector for the creation of mammalian cell lines that predisposes all neomycin resistant cells to express recombinant protein (see Rees S., Coote J., Stable J., Goodson S., Harris S. & Lee M. G. (1996) Biotechniques, 20, 102-112) by virtue of the recombinant cDNA being linked to the neomycin-selectable marker cDNA downstream of the CMV promoter (for full details see Chen Y H, Dale T J, Romanos M A, Whitaker W R, Xie X M, Clare J J. Cloning, distribution and functional analysis of the type III sodium channel from human brain Eur J Neurosci, 2000 December; 12, 4281-9). Cells were cultured in Iscove's modified Dulbecco's medium (Invitrogen) comprising, 10% fetal bovine serum, 1% L-glutamine, 1% Penicillin-Streptomycin (Invitrogen), 1% non-essential amino acids, 2% H-T supplement and 1% G418 (Invitrogen) and maintained at 37° C. in a humidified environment comprising 5% CO2 in air. Cells were liberated from the T175 culture flask for passage and harvesting using Versene (Invitrogen).

Cell Preparation

Cells were grown to 60-95% confluence in a T75 flask. Cells were lifted by removing the growth media and incubating with 1.5 ml of warmed (37° C.) Versene (Invitrogen, 15040-066) for 6 min. Lifted cells were suspended in 10 ml of PBS (Invitrogen, 14040-133). Cell suspension was then placed into a 10-ml centrifuge tube and centrifuged for 2 min at 700 rpm. After centrifugation, the supernatant was removed and the cell pellet was resuspended in 3 ml of PBS.

Electrophysiology

Currents were recorded at room temperature (21-23° C.) using the IonWorksHT planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential of −90 mV to 0 mV were applied for 20 ms and repeated 10 times at a frequency of 10 Hz. In all experiments, the test pulse protocol was performed in the absence (pre-read) and presence (post-read) of a compound. Pre- and post-reads were separated by a compound addition followed by a 3-3.5 min incubation.

Solutions and Drugs

The intracellular solution contained the following (in mM): K-gluconate 100, KCl 40 mM, MgCl2 3.2, EGTA 3, HEPES 5, adjusted to pH 7.25. Amphotericin was prepared as 30 mg/ml stock solution and diluted to a final working concentration of 0.1 mg/ml in internal buffer solution. The external solution was Dulbecco's PBS (Invitrogen) and contained the following (in mM): CaCl2 0.90, KCl 2.67, K3PO4 1.47, MgCl2 0.50, NaCl 138, Na3PO4 8.10, with a pH of 7.4. Compounds were prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analysed and filtered using both seal resistance (>40 MΩ) and peak current amplitude (>200 pA) in the absence of compound to eliminate unsuitable cells from further analysis. Paired comparisons between pre-drug and post-drug additions were used to determine the inhibitory effect of each compound. The concentrations of compounds required to inhibit current elicited by the $1^{st}$ depolarising pulse by 50% (tonic pIC50) were determined by fitting of the Hill equation to the concentration response data. In addition the use-dependent inhibitory properties of the compounds were determined by assessing the effect of compounds on the $10^{th}$ versus $1^{st}$ depolarising pulse. The ratio of the $10^{th}$ over $1^{st}$ pulse was calculated in the absence and presence of drug and the % use-dependent inhibition calculated. The data was fitted using the same equation as for the tonic $pIC_{50}$ and the concentration producing 15% inhibition (use-dependent $pUD_{15}$) calculated.

PreClinical Experiments

Rat MEST Model

Experimental Preparation

This work was conducted in compliance with the Home Office Guidance on the operation of the Animals (Scientific Procedures) Act 1986 and GlaxoSmithKline ethical standards. Male CD rats (100-145 g) were supplied by Charles River, UK. Animals were group housed (6 animal per cage) with free access to food (Standard rodent chow; Harlan, UK) and water under a 12 h light/dark cycle (lights on at 0700 h). A period of at least one week between arrival at GSK and the study was allowed in all cases.

Experimental Protocol

Animals were administered a test compound at the appropriate dose, route and pre-treatment time and returned to their home cage. Testing occurred in a separate room from that used for housing. Testing involved determining the threshold for tonic hindlimb extensor seizures using a Hugo Sachs Electronik stimulator which delivers a constant current of 0.3 second duration, 50 Hz, sinewave form, fully adjustable between 1 and 300 mA. Stimuli were delivered via corneal electrodes (Stean T O, Atkins A R, Heidbreder C A, Quinn L P, Trail B K, Upton N. (2005) Br J. Pharmacol. 144(5):628-35). Seizure threshold was determined using the 'up and down' method of Kimball et al. (1957)(Kimball A W, Burnett W T Jr, Doherty D G. (1957) Radiat Res. 7(1):1-12). The first animal tested in each group was stimulated with a current that might be expected to be close to the threshold for induction of a seizure. If a tonic seizure was not induced, then then next animal in the group received a stimulus 5 mA higher. If a tonic seizure was induced, then the next animal received a stimulus 5 mA lower. This is repeated for all animals within the control (vehicle) group. In the case of groups treated with a sodium channel blocker steps of 10 to 30 mA were used.

Satellite animals (n=3/group) received the same drugs or combinations of drugs as the test groups, and were culled at the appropriate time after dosing. Blood and brain samples were taken for analysis of the drug concentrations in these compartments.

Drugs and Materials

All doses were calculated as base. ENa9 and ENa13 were dosed via the subcutaneous (s.c.) route at 1 ml/kg in a 2% v/v DMSO/saline vehicle 30 minutes prior to test. ENa7 and ENa14 were dosed orally (p.o.) in a 1% w/v methylcellulose/water vehicle at 2 ml/kg, 60 minutes before test. Compound ENK6 was dosed with via the intraperitoneal (i.p.) route 60 minutes before the test or via the s.c. route 15 minutes before test. In both cases ENK6 was dissolved in saline.

Data Analysis

Induction of seizure is measured as an all-or-nothing effect scored as either present (+) or absent (0) for each animal. The data for each treatment group were recorded as the number of +'s and 0's at each current level employed and this information was then used to calculate the CC50 value (current required for 50% of animals to show seizure behaviour)+ standard error of the mean according to the method of Kimball et al. (1957). Drug effects were calculated as the % change in CC50. Significant differences between drug-treated animals and appropriate vehicle treated groups were assessed according to the methods of Litchfield and Wilcoxon (1949). The statistical significance of differences between sodium channel blocker alone or in combination with ENK6 was assessed using a Student's t test.

ENa9/ENK6 Combination

A dose of 3 mg/kg s.c. of ENa9 gave a small, but significant increase in seizure threshold in the MEST, whereas a lower dose of 1 mg/kg s.c. was inactive. ENK6 (30 mg/kg i.p.) had no effect on seizure threshold when administered alone. However, in the presence of ENK6, ENa9 significantly increased seizure threshold at the low dose of 1 mg/kg s.c. (133% increase in CC50(mA)) and produced a significantly larger increase at 3 mg/kg s.c. (323% increase in CC50(mA)) (FIG. 1).

No increase in blood or brain concentration of ENa9 was observed in the presence of ENK6 (Table 1), suggesting that a PK interaction does not explain the increased PD effect.

TABLE 1

Table 1: Blood and brain concentrations of ENa9 and ENK6 in satellite animals (n = 2 per group, except *n = 1). Small differences in exposure are within inter-animal variability.

| ENK6 (mg/kg) | ENa9 (mg/kg) | Blood (ng/mL) ENK6 | Blood (ng/mL) ENa9 | Brain (ng/g) ENK6 | Brain (ng/g) ENa9 |
|---|---|---|---|---|---|
| veh | 1 | | 188 | | 1171 |
| veh | 3 | | 349 | | 2301 |
| 30 | veh | 631* | | 1506* | |
| 30 | 1 | 471 | 246 | 1162 | 1339 |
| 30 | 3 | 414 | 456 | 881 | 2621 |

ENa13/ENK6 Combination

Figure 2:
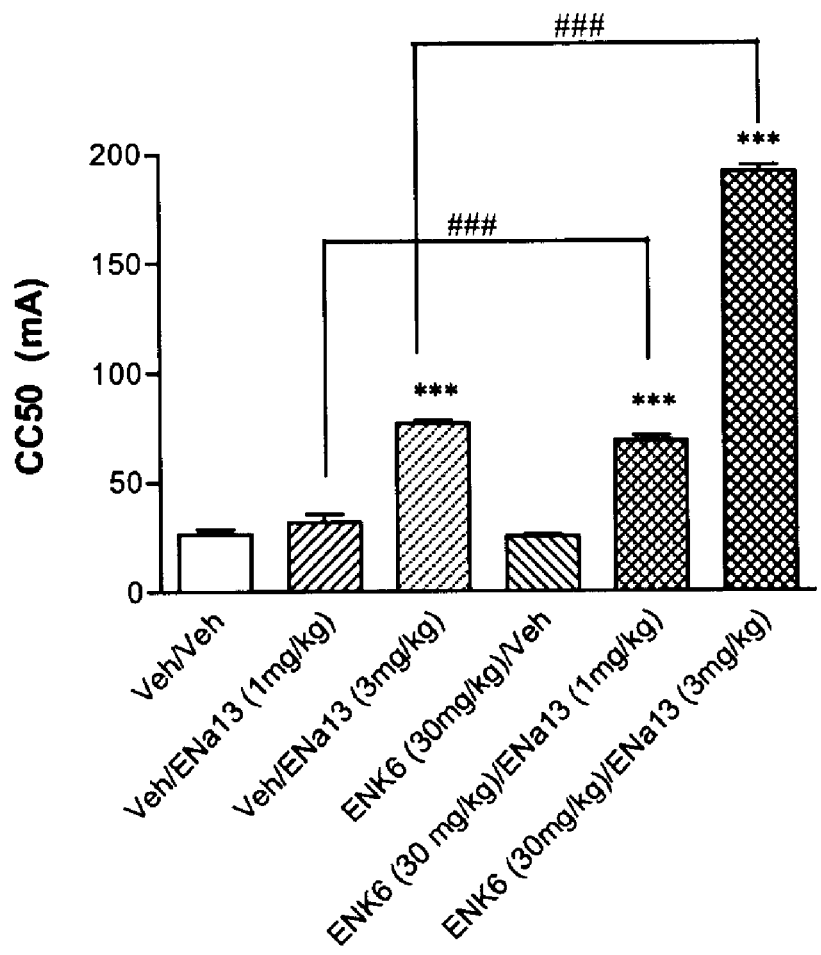
FIG. 2: Effects of ENa13 and ENK6 in the rat MEST model. ENK6 (30 mg/kg, ip, 60 min ptt); GSK1061436A (1.0 & 3.0 mg/kg, sc, 30 min ptt). ***$p<0.001$ vs corr vehicle, Wilcoxon Test; ### $p<0.001$ Vs corr vehicle/ENa13, t-test.

A dose of 3 mg/kg s.c. of ENa13 was found to give a robust and significant increase in seizure threshold, whereas a lower dose of 1 mg/kg s.c. was inactive. ENK6 (30 mg/kg i.p.) had no effect on seizure threshold when administered alone. In the presence of ENK6, ENa13 produced a significant increase in seizure threshold at 1 mg/kg (118% increase in CC50(mA)) and also a significant increase in seizure threshold at 3 mg/kg (129% increase in CC50(mA)) (FIG. 2).

No increase in the concentration of ENa13 was observed in the presence of the NK1 antagonist (Table 2); suggesting that a PK interaction does not explain the increased PD effect.

TABLE 2

Table 2: Blood and brain concentrations of ENa13 and ENK6 in satellite animals (n = 2 per group, except *n = 1). Differences in concentrations of the sodium channel blocker are within inter-animal variability.

| ENK6 (mg/kg) | ENa13 (mg/kg) | Blood (ng/mL) ENK6 | Blood (ng/mL) ENa13 | Brain (ng/g) ENK6 | Brain (ng/g) ENa13 |
|---|---|---|---|---|---|
| veh | 1 | | 499 | | 478 |
| veh | 3 | | 1824 | | 1825 |
| 30 | veh | 558* | | 1263* | |
| 30 | 1 | 456 | 416 | 1035 | 508 |
| 30 | 3 | 1209 | 1160 | 4802 | 1235 |

ENa7/ENK6 Combination

Figure 3:
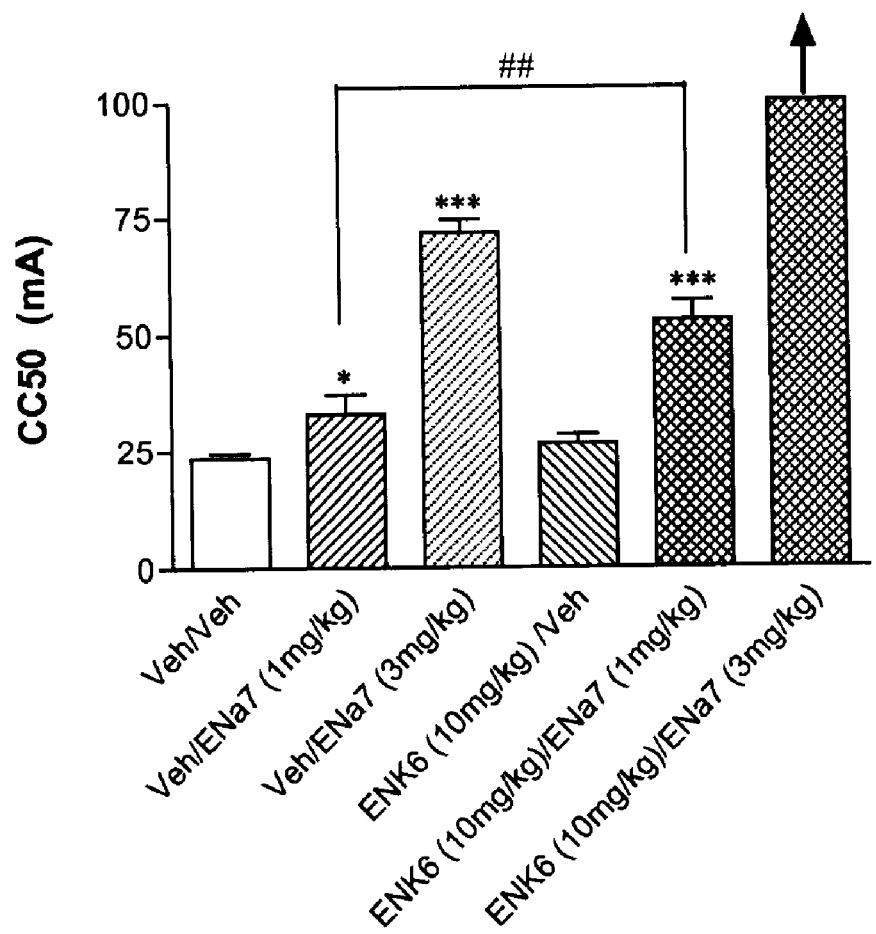
FIG. 3: Effects of ENa7 and ENK6 (10 mg/kg s.c.) in the rat MEST model. ENK6 (10 mg/kg, sc, 15 min ptt); Ena7 (1 & 3 mg/kg, po, 60 min ptt). The vertical arrow indicates that the CC50 value could not be determined, but was greater than 180 mA (>780% increase). *p<0.05, ***p<0.001 vs corr vehicle, Wilcoxon Test. ##p<0.01 Vs corr vehicle/ENa7 group, t-test.
Figure 4:
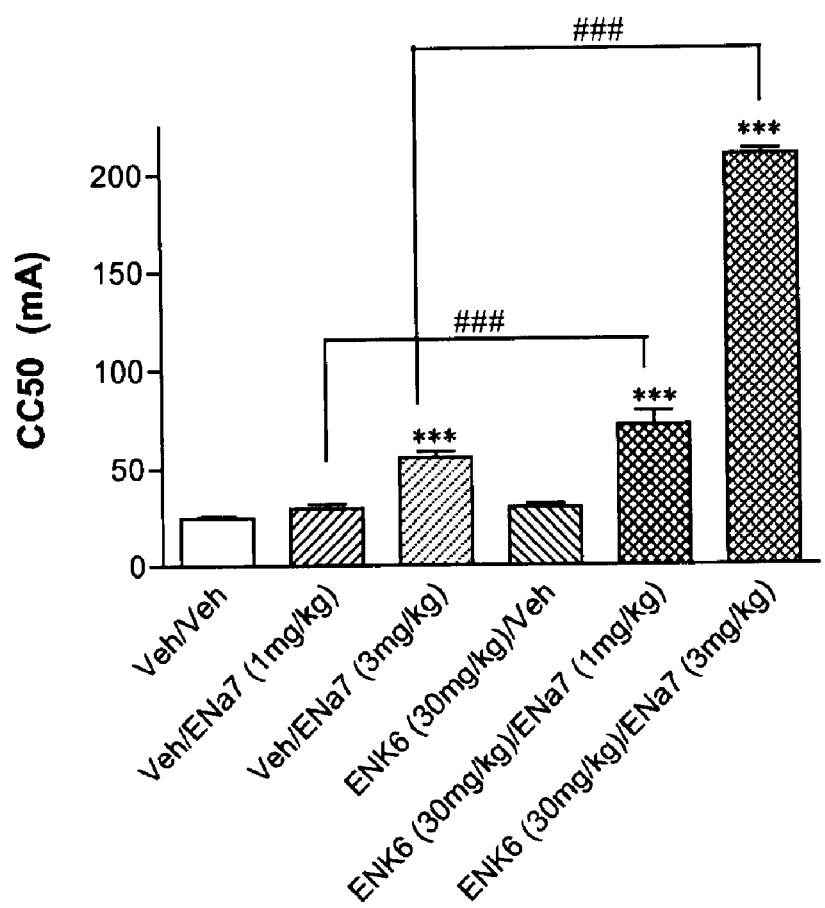
FIG. 4: Effects of ENa7 and ENK6 (30 mg/kg s.c.) in the rat MEST model. ENK6 (30 mg/kg, sc, 15 min ptt); Ena7 (1 & 3 mg/kg, po, 60 min ptt). ***p<0.001 vs corr vehicle, Wilcoxon Test. ### p<0.001 Vs corr vehicle/ENa7 group, t-test.

ENa7 was administered orally to rats 60 minutes before the test, whereas ENK6 was administered subcutaneously 15 minutes before testing. Satellite animals were similarly dosed to provide estimates of blood and brain concentrations of the two drugs. A dose of 1 mg/kg p.o. of lamotrigine was tested, as well as a dose of 3 mg/kg p.o. Two independent experiments were conducted, the first using 10 mg/kg s.c. of ENK6 and the second using 30 mg/kg s.c. of ENK6. In each experiment ENK6 alone had no effect on seizure threshold, whereas as expected, ENa7 alone at 1 mg/kg produced little or no increase in seizure threshold, the higher dose of 3 mg/kg significantly increased seizure threshold by 128-205%. In the presence of ENK6, lamotrigine significantly increased seizure threshold at the dose of 1 mg/kg (61% increase in CC50 (mA) in the first experiment and 145% increase in CC50(mA) in the second experiment), and produced a near-maximal increase in threshold with the dose of 3 mg/kg (233% increase in CC50(mA) in the second experiment) (FIGS. 3 & 4). Blood and brain concentrations of ENa7, measured in satellite animals, are reported in Tables 3 & 4.

Blood and brain concentrations of ENa7, measured in satellite animals, are reported in Tables 3 & 4.

TABLE 3

Table 3: Blood and brain concentrations of ENa7 and ENK6 in satellite animals (n = 2-3 per group, except *n = 1). Differences in concentrations of the sodium channel blocker are within inter-animal variability.

| ENK6 (mg/kg) | ENa7 (mg/kg) | Blood (ng/mL) ENK6 | Blood (ng/mL) ENa7 | Brain (ng/g) ENK6 | Brain (ng/g) ENa7 |
|---|---|---|---|---|---|
| veh | 1 | — | 311* | — | 517* |
| veh | 3 | — | 1180* | — | 2829* |
| 10 | veh | 839 | — | 1420 | — |
| 10 | 1 | 635 | 581 | 1254 | 1125 |
| 10 | 3 | 732 | 1603 | 1504 | 2855 |

TABLE 4

Table 4: Blood and brain concentrations of ENa7 and ENK6 in satellite animals (n = 2 per group except *n = 1). Differences in concentrations of the sodium channel blocker are within inter-animal variability.

| ENK6 (mg/kg) | ENa7 (mg/kg) | Blood (ng/mL) ENK6 | Blood (ng/mL) ENa7 | Brain (ng/g) ENK6 | Brain (ng/g) ENa7 |
|---|---|---|---|---|---|
| veh | 1 | — | 352* | — | 588* |
| veh | 3 | — | 1354* | — | 2192* |
| 30 | veh | 1886 | — | 4495 | — |
| 30 | 1 | 1542 | 461 | 3343 | 752 |
| 30 | 3 | 1481 | 1404 | 2484 | 2096 |

ENa15+ENK6

Figure 5:
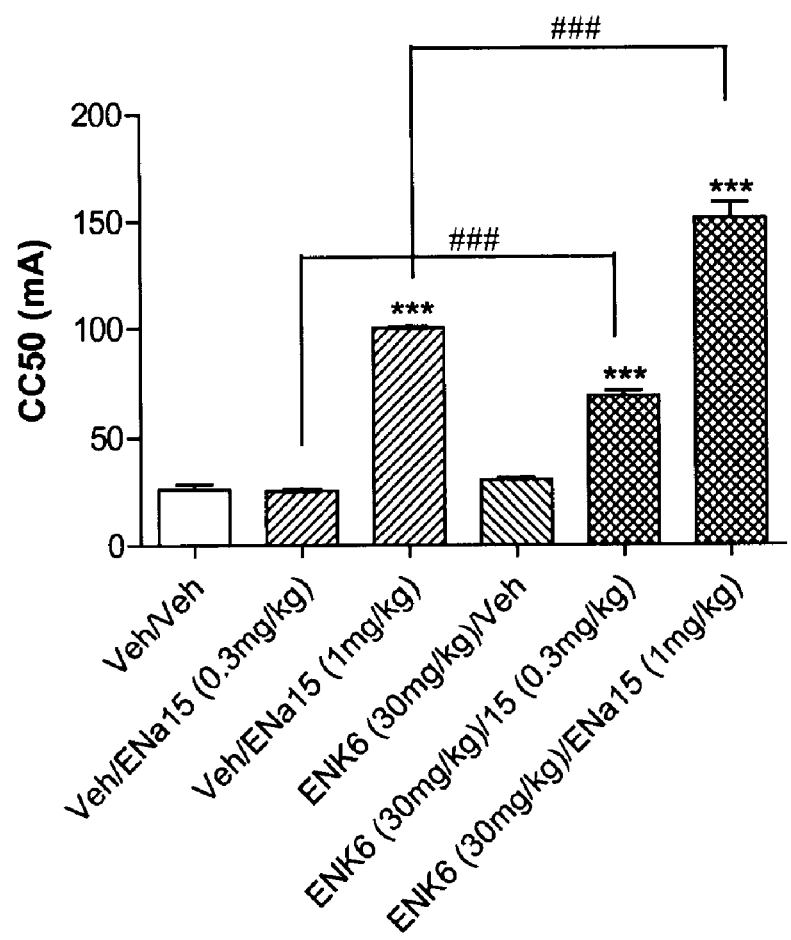
FIG. 5: Effects of ENa15 and ENK6 (30 mg/kg s.c.) in the rat MEST model. ENK6 (30 mg/kg, sc, 15 min ptt); ENa15 (0.3 & 1 mg/kg, po, 60 min ptt). ***p<0.001 vs corr vehicle, Wilcoxon Test. ### p<0.001 Vs corr vehicle/ENa15 group, t-test.

ENa15 was administered orally to rats 60 minutes before the test, ENK6 (30 mg/kg) was administered subcutaneously 15 minutes before testing. Satellite animals were similarly dosed to provide estimates of blood and brain concentrations of the two drugs. A dose of 0.3 mg/kg p.o. of ENa15 was tested, as well as a dose of 1 mg/kg p.o. ENK6 alone had no effect on seizure threshold. ENa15 alone at 0.3 mg/kg produced no increase in seizure threshold, whereas the higher dose of 1 mg/kg significantly increased seizure threshold by 292%. In the presence of ENK6, ENa15 significantly increased seizure threshold at the previously inactive dose of 0.3 mg/kg (176% increase in CC50(mA)), and also produced a significant increase in threshold at 1 mg/kg (51% increase in CC50(mA)) (FIG. 5).

FCA (Freunds Complete Adjuvant) Model of Inflammatory Hypersensitivity to Pain

This following series of studies demonstrates that the combination of a Sodium Channel compound (ENa7) and an NK1 antagonist (ENK6) produces a synergistic effect in the FCA model of inflammatory hypersensitivity to pain:
a) the effect of ENa7 alone and ENK6 alone on the FCA induced hypersensitivity to pain is tested; the purpose of this study is to determine the ED20 dose for the combination study;
b) then the combination of ENa7 and ENK6 (ED20 doses) on the FCA induced hypersensitivity is evaluated;
c) combination of ENa7 and ENK6 as fixed dose ratio (1:1.25) on the FCA induced hypersensitivity to pain is evaluated.

a) The effect of ENa7 Alone and ENK6 Alone on the FCA Induced Hypersensitivity to Pain Method Naïve weight bearing readings were taken. The hypersensitivity to pain was measured using the Rat incapacitance tester (Linton instruments). This instrument is serviced once a year and should be regularly calibrated All rats then received an intraplantar injection of 100 ul of FCA (Freund's complete adjuvant) into the left hind paw. The FCA was sonicated for 15 minutes prior to use.

Approximately 23 hrs after administration of the FCA, pre-dose weight bearing readings were taken. All animals were then ranked and randomised for dosing according to their FCA window (predose difference in grams–naïve difference in grams). Rats with FCA window less than 30 g were excluded from the study.

Animals were then dosed with vehicle (1% methylcellulose) s.c or, ENK6 0.1-3 mgkg s.c or ENa7 0.1-3 mg/kg p.o. Celebrex 10 mg/kg p.o. (positive control) as appropriate according to ranking and randomisation.

Animals were assessed in the weight bearing apparatus 1 hour post dose.

The study was blind and randomised by FCA window using the Latin square method.

% reversals were calculated by using the naïve, pre-dose and post dose values as follows: % Reversal=[(Pre-dose−Post-dose)/(Pre-dose−Naïve)]×100

Graphs and ED50 were calculated where appropriate using Prism4.

Statistical analysis was carried out using ANOVA followed by calculating the least square means using the statistical package Statistica 6.1

From the dose response curves the ED20 was determined for the combination study

Results

Effect of ENa7 Alone on the FCA Induced Hypersensitivity to Pain

Figure 6:
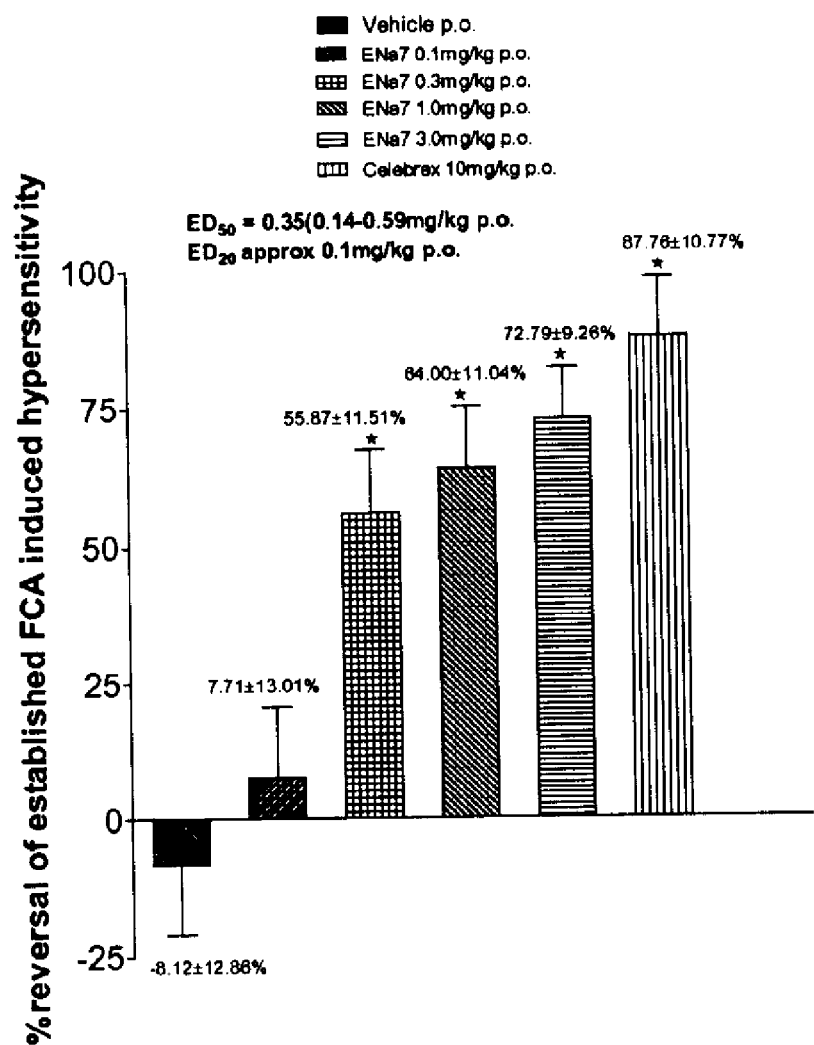
FIG. 6: Effect of ENa7 alone on the FCA induced hypersensitivity to pain

ENa7 (0.1-3.0 mg/kg p.o,) produced a dose related reversal of the FCA induced hypersensitivity with an ED50 of 0.35 (0.14-0.59)mg/kg p.o. The ED20 was 0.2 mg/kg p.o. (FIG. 6).

Effect of ENK6 Alone on the FCA Induced Hypersensitivity to Pain

Figure 7:
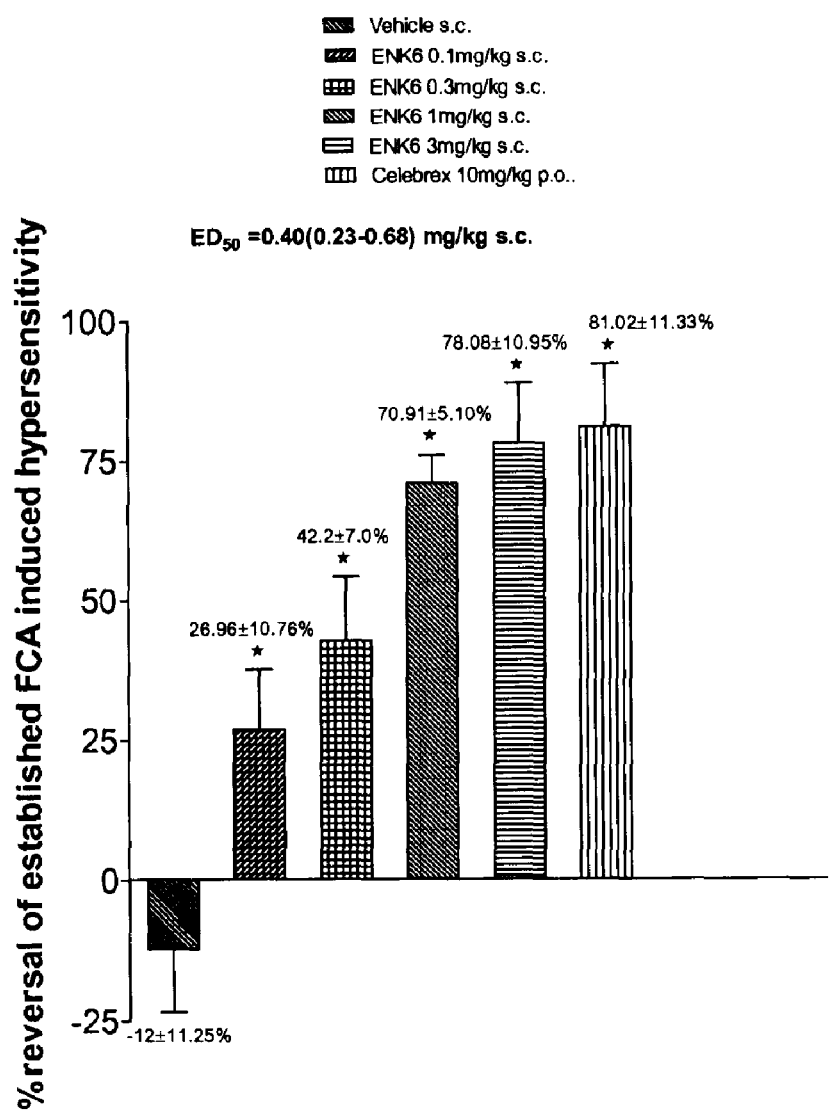
FIG. 7: Effect of ENK6 alone on the FCA induced hypersensitivity to pain.

ENK6 (0.1-3.0 mg/kg p.o.) produced a dose related reversal of the FCA induced hypersensitivity with an ED50 of 0.40 (0.23-0.68)mg/kg p.o. The ED20 was calculated to be 0.08 mg/kg p.o.
(FIG. 7)

The fixed dose ratio is therefore calculated to be 1.25:1. This ratio is used to calculate the doses for the fixed dose ratio studies.

b) The Effect of Combination of ENa7 and ENK6 (ED20 Doses) on the FCA Induced Hypersensitivity to Pain Method Naïve weight bearing readings were taken. The hypersensitivity to pain was measured using the Rat incapacitance tester (Linton instruments). This instrument is serviced once a year and should be regularly calibrated All rats then received an intraplantar injection of 100 ul of FCA (Freund's complete adjuvant) into the left hind paw. The FCA was sonicated for 15 minutes prior to use.

Approximately 23 hrs after administration of the FCA, pre-dose weight bearing readings were taken. All animals were then ranked and randomised for dosing according to their FCA window (predose difference in grams–naïve difference in grams). Rats with FCA window less than 30 g were excluded from the study.

Animals were then dosed with vehicle with vehicle p.o. or ENa7 0.1 mg/kg p.o. 30 mins later animals were dose again with Vehicle or ENK6 0.08 mg/kg s.c. according to ranking and randomisation. See table 5 for details of the groups Animals were assessed in the weight bearing apparatus 1 hour post dose.

The study was blind and randomised by FCA window using the Latin square method.

% reversals were calculated by using the naïve, pre-dose and post dose values as follows: % Reversal=[(Pre-dose−Post-dose)/(Pre-dose−Naïve)]×100

Statistical analysis was carried out using ANOVA followed by calculating the least square means using the statistical package Statistica 6.1

ED50 and ED20 values and graphs were calculated using prism5

TABLE 5

| Treatment | Dose mg/kg | Dose vol. | Route | n | group |
|---|---|---|---|---|---|
| 100 μl FCA + Vehicle p.o. 30 mins later Vehicle s.c.. | — | 5 | p.o. | 6 | A |
| 100 μl FCA + ENa7 0.1 mg/kg p.o. 30 mins later Vehicle s.c. |  | 5 | p.o. | 6 | B |
| 100 μl FCA + Vehicle p.o. 30 mins later ENK6 0.08 mg/kg s.c. |  | 5 | p.o. | 6 | C |
| 100 μl FCA + Lamotrigine 30 mins later ENa7 |  | 5 | p.o. | 6 | D |
| 100 μl FCA + Vehicle p.o. 30 mins later Celebrex 10 mg/kg p.o. |  | 5 | p.o | 6 | E |

Results

Figure 8:
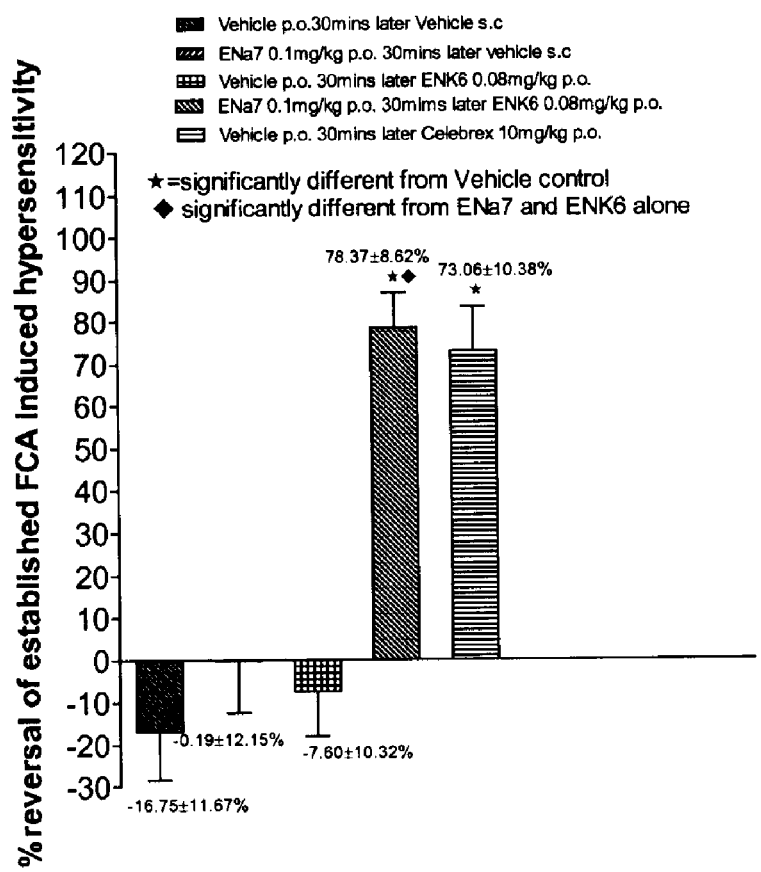
FIG. 8: Effect combination of ENa7 and ENK6 (ED20doses) on the FCA induced hypersensitivity to pain.

Effect Combination of ENa7 and ENK6 (ED20 Doses) on the FCA Induced Hypersensitivity to Pain The combination study used a dose of ENa7 of 0.1 mg/kg p.o. and ENK6 0.08 mg/kg p.o. (ED20 doses); the combination produced a marked reversal of the FCA induced hypersensitivity which was at least additive. (FIG. 8)

c) Method for Testing ENa7/ENK6 Combination at a Fixed Dose Ratio (1:1.25)

Naïve weight bearing readings were taken. The hypersensitivity to pain was measured using the Rat incapacitance tester (Linton instruments). This instrument is serviced once a year and should be regularly calibrated All rats then received an intraplantar injection of 100 ul of FCA (Freund's complete adjuvant) into the left hind paw. The FCA was sonicated for 15 minutes prior to use.

Approximately 23 hrs after administration of the FCA, pre-dose weight bearing readings were taken. All animals were then ranked and randomised for dosing according to their FCA window (predose difference in grams–naïve difference in grams). Rats with FCA window less than 30 g were excluded from the study.

Animals were then dosed with the following in a fixed dose ratio of 1.25:1 according to ranking and randomisation. (Table 6)

TABLE 6

| Treatment<br>Fixed dose ratio 1.25:1 | n | group |
|---|---|---|
| 100 µl FCA + Vehicle p.o 30 mins later Vehicle s.c. | 6 | A |
| 100 µl FCA + ENa7 0.1 mg/kg p.o 30 mins later ENK6 0.08 mg/kg s.c | 6 | B |
| 100 µl FCA + ENa7 0.03 mg/kg p.o. 30 mins later ENK6 0.024 mg/kg s.c. | 6 | C |
| 100 µl FCA + ENa7 0.01 mg/kg p.o. 30 mins later ENK6 0.008 mg/kg s.c | 6 | D |
| 100 µl FCA + ENa7 0.003 mg/kg p.o. 30 mins later ENK6 0.0024 mg/kg s.c. | 6 | E |
| 100 µl FCA + Vehicle p.o 30 mins later Celebrex 10 mg/kg p.o. | 6 | F |

Animals were assessed in the weight bearing apparatus 1 hour post dose.

The study was blind and randomised by FCA window using the Latin square method.

% reversals were calculated by using the naïve, pre-dose and post dose values as follows: % Reversal=[(Pre-dose−Post-dose)/(Pre-dose−Naïve)]×100

The data was analysed using the FCA macro written in excel (version 1.5) developed by Paul Lloyd. Graphs and ED50 were calculated where appropriate using Prism5

Statistical analysis was carried out using ANOVA followed by calculating the least square means using the statistical package Statistica 6.1

Results

Figure 9:
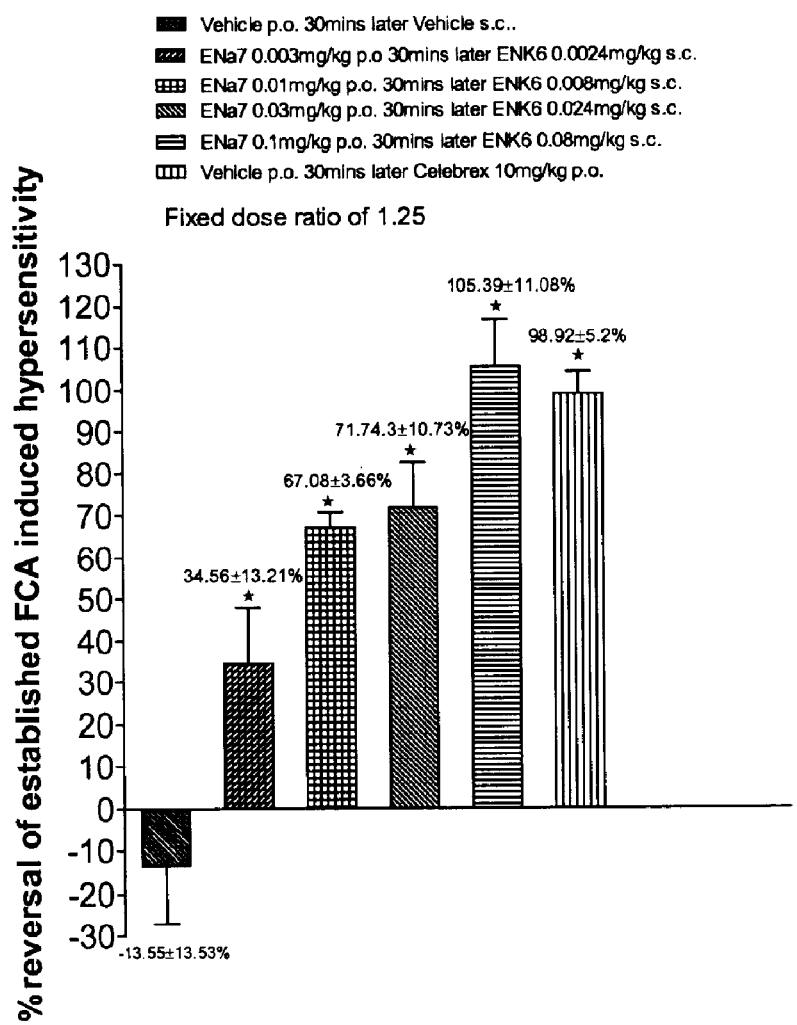
FIG. 9: Effect combination of ENa7 and ENK6 (Fixed dose ratio 1.25:1) on the FCA induced hypersensitivity to pain.

Effect Combination of ENa7 and ENK6 (Fixed Dose Ratio 1.25:1) on the FCA Induced Hypersensitivity to Pain The combination of ENa7 and ENK6 produced a dose related reversal of the FCA induced hypersensitivity. Analysis of the data using Statistica demonstrated that this effect was highly synergistic (FIG. 9).

Summary of Results

ENK6 produces a dose related reversal of FCA induced hypersensitivity. ED20 is calculated to be approx 0.08 mg/kg s.c ENa7 produces a dose related reversal of FCA induced hypersensitivity. ED20 is calculated to be approx 0.1 mg/kg p.o.

The ED20's of ENa7 and ENK6 has no significant effect on the FCA induced hypersensitivity The combination of ENa7 and ENK6 produces a very marked reversal of FCA induced hypersensitivity which is not significantly different to Celebrex; the effect is at least additive.

The fixed dose ratio is 1.25; the fixed dose ratio study shows there is highly significant synergy when ENa7 is combined with the NK1 antagonist ENK6.

Thus, the data show that ENa7 in combination with ENK6 produces a highly synergistic effect.

The invention claimed is:

1. A pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt thereof, and a sodium channel blocker wherein the sodium channel blocker is selected from lamotrigine;
   (5R)-5-(4-{[(2-fluorophenyl)methyl]oxy}phenyl)-L-prolinamide;
   2R,5R)-2-(4-{[(2-fluorophenyl)methyl]oxy}phenyl)-7-methyl-1,7-diazaspiro[4.4]nonan-6-one;
   R(−)-2,4-diamino-5-(2,3-dichlorophenyl)-6-fluoromethyl pyrimidine;
   and pharmaceutically acceptable salts thereof;
   as a combined preparation for simultaneous or sequential administration.

2. A pharmaceutical composition comprising the NK1 receptor antagonist [2-Methoxy-5-(5-trifluoromethyl-tetrazol-1-yl)-benzyl]-(2S-phenyl-piperidin-3S-yl)-amine, or a pharmaceutically acceptable salt thereof, and a sodium channel blocker wherein the sodium channel blocker is selected from lamotrigine;
   (5R)-5-(4-{[(2-fluorophenyl)methyl]oxy}phenyl)-L-prolinamide;
   (2R,5R)-2-(4-{[(2-fluorophenyl)methyl]oxy}phenyl)-7-methyl-1,7-diazaspiro[4.4]nonan-6-one;
   R(−)-2,4-diamino-5-(2,3-dichlorophenyl)-6-fluoromethyl pyrimidine;
   and pharmaceutically acceptable salts thereof;
   as a combined preparation for simultaneous or sequential administration, wherein at least one of the components selected from [2-Methoxy-5-(5-trifluoromethyl-tetrazol-1-yl)-benzyl]-(2S-phenyl-piperidin-3S-yl)-amine and the sodium channel blocker is at subtherapeutic dose.

3. A method of treating a human subject affected by epilepsy or a mood disorder, said method comprising administering to said human subject a pharmaceutical composition according to claim 1.

4. A method of treating a human subject affected by epilepsy or a mood disorder, said method comprising administering to said human subject a pharmaceutical composition according to claim 2.

* * * * *